United States Patent [19]

Serfontein

[11] Patent Number: 5,254,572
[45] Date of Patent: Oct. 19, 1993

[54] METHOD AND COMPOSITION FOR SUPPLEMENTING VITAMIN B6 WHERE THE PN-PLP PATHWAY IS DISTURBED

[75] Inventor: Willem J. Serfontein, Pretoria, South Africa

[73] Assignee: Vesta Medicines (pty) Ltd., South Africa

[21] Appl. No.: 466,676

[22] Filed: Jan. 17, 1990

Related U.S. Application Data

[63] Continuation-in-part of Ser. No. 125,996, Nov. 27, 1987, abandoned, and Ser. No. 395,033, Aug. 17, 1989, abandoned, which is a continuation-in-part of Ser. No. 125,996, Aug. 17, 1989, and Ser. No. 153,973, Feb. 9, 1988, abandoned.

[30] Foreign Application Priority Data

Jan. 17, 1989 [GB] United Kingdom ................ 8900924

[51] Int. Cl.$^5$ ............................................. A61K 31/44
[52] U.S. Cl. .................................... 514/345; 514/351
[58] Field of Search ................................ 514/345, 351

[56] References Cited

FOREIGN PATENT DOCUMENTS 1478560 7/1977 Switzerland .

*Primary Examiner*—Zohreh A. Fay
*Attorney, Agent, or Firm*—Omri M. Behr; Matthew J. McDonald

[57] ABSTRACT

Treatment or prophylaxis of depressed or inadequate intracellular pyridoxal phosphate levels in a human or animal patient resulting from a condition, wherein the pyridoxihe (PN)—pyridoxal phosphate (PLP) pathway is disturbed or insufficient, either by chemical factors as occur in physiological shock myocardial, infarction, release of polyamines or toxins by cell death or microbes, vitamin B6 antagonistic drugs; or by enzymatic insufficiencies inherent in the cells of a patient caused by genetic lack of oxidase or genetic oxidase polymorphism; cellular immaturity of premature infants; in conditions involving anemia, destruction of erythrocytes (e.g. malaria, biliary fever). The deficiencies are counteracted by the administration of pyridoxal or a precursor of pyridoxal which in vivo, once it has entered the bloodstream, is rapidly converted into pyridoxal without the intervention of oxidase or oxygen, optionally and preferably without the intervention of kinase.

8 Claims, No Drawings

METHOD AND COMPOSITION FOR SUPPLEMENTING VITAMIN B6 WHERE THE PN-PLP PATHWAY IS DISTURBED

RELATED APPLICATIONS

This is a continuation-in-part of U.S. Ser. No. 07 125,996 dated Nov. 27, 1987, now abandoned, and of U.S. Ser. No. 07/395,033 dated Aug. 17, 1989, now abandoned, which is likewise a continuation-in-part of U.S. Ser. No. 07/125,996 and which is also a CIP of U.S. Ser. No. 07/153,973 (now abandoned), dated Feb. 9, 1988.

The present invention relates to pharmaceutical, veterinary or dietary compositions and the use thereof for a method of treatment or prophylaxis of depressed or inadequate intracellular pyridoxal phosphate levels in a human or animal patient resulting from a condition, wherein the pyridoxine (PN)—pyridoxal phosphate (PLP) pathway is disturbed or insufficient. The invention also provides new diagnostic methods and means for diagnosing such depressed or inadequate pyridoxal phosphate levels or disturbance in the pathway, more particularly for use in conjunction with the said treatment or prophylaxis.

DISCUSSION OF PRIOR ART

The vital role of vitamin B6 (hereinafter abbreviated to B6) in health and disease has been extensively researched over the past two decades. It is now realised that many serious diseases and clinical conditions are associated with reduced blood and cellular vitamin B6 activity. However, until now many of the physiological interrelationships in animals and humans have not been known or understood. In particular there has been confusion as to whether observations relating to vitamin B6 and B6 vitamer deficiencies were results of clinical conditions or whether these deficiencies were causally related to the clinical conditions. This was due inter alia to a disregard of certain aspects of the pharmacokinetics involved, and of the role of different B6 vitamers. Prior to the present invention certain of these vitamers had never been determined systematically in biological fluids during disease processes, and indeed no suitable routine methods had existed for such systematic determinations.

It is known that vitamin B6 occurs in three primary forms, known by their trivial names: pyridoxine (PN, formula I), pyridoxal (PL, formula II) and pyridoxamine (PM, formula III) as well as the corresponding phosphorylated forms PNP, PLP and PMP. Of these, PN is the form exclusively used commercially in pharmaceutical formulations up till now. It is also the main B6 vitamer in plants.

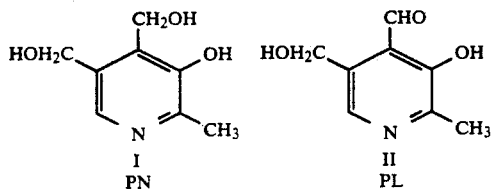

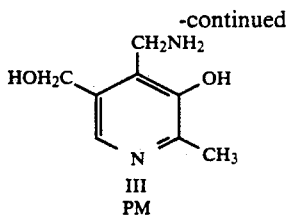

Inside living human and animal cells, PLP is the biologically active form of vitamin B6, acting as coenzyme in more than 100 biological reactions.

Pharmaceutical compositions for the aforesaid purposes, comprising B6 in the form of PL had not been proposed prior to the priority date of the parent application and had not been available previously. In fact, there has been a distinct prejudice in the art against the administration of B6 in any form other than that of PN. That prejudice was based not only on cost but also on the relative stability and longer shelf-life of PN. IN vitro PL is less stable. In short, there existed and still exists a severe prejudice in the art against the use of B6 vitamers other than the conventional PN such that persons skilled in the art were disinclined to accept that such other vitamers could offer any worthwhile advantages.

French patent specification 50 871 teaches compositions specifically for cardiac complaints comprising a combination of two active ingredients one being theophylline or one of certain derivatives thereof or camphor derivatives or digitalis and the other being vitamin B6. Although the specification states that vitamin B6 can be employed in the form of any of its aforesaid vitamers, the enabling disclosure, in particular that of the examples, is restricted to pyridoxine. No explanation is given of the therapeutic mechanism. Indeed the rationale behind the teachings of the reference is obscure, because it is said that the vitamin B6 as such has no effect on cardiac function. No teachings relating to the purposes and therapeutic effects contemplated by the present invention can be extracted from that French patent when read in the light of the knowledge in the art at the time. In particular the French patent does not teach the administration of vitamin B6 for the treatment or prophylaxis of actually depressed or inadequate intracellular PLP levels. Disturbances of the PN-PLP pathway are neither referred to nor suggested.

The present invention is based on extensive research which has brought to light a large number of clinical or pathological conditions in animals or man associated with depressed or inadequate intracellular pyridoxal phosphate levels, resulting from factors whereby the pyridoxine-pyridoxal phosphate pathway is disturbed or rendered insufficient.

However, surprisingly the conventional manners of administration of PN frequently do not lead to the desired alleviation of B6 deficiencies in blood plasma and in living cells, inter alia in critically ill patients. The consequences of such deficiencies can be most severe. Neither the extent of these consequences nor the causes thereof had been appreciated in the past, or adequately so. As will be explained further below, these B6 deficiencies are on the one hand caused or aggravated by a variety of physiological factors. They are in turn themselves the cause of a downbreak of vital physiological functions, which is often fatal. Many important drugs used in the treatment of diseases, whilst combatting the primary symptoms and/or causes of such diseases, have now been identified as severe contributors to B6 deficiencies which have unwittingly aggravated this downbreak of physiological functions. The administration of PN at best achieves partial and relatively slow alleviation of the B6 deficiency, and often not at all, particularly in the severely ill patient. The problem cannot be overcome by increasing the dosage of PN for reasons now established for the first time by us and explained in greater detail below.

A recent German application (P 37 05 549.6) having a date later than that of the parent application hereof teaches the use of pyridoxal, pyridoxamine and their phosphates for the regulation of cholesterol levels and lipid compositions in serum. The specification contains no teachings pertaining to the uses herein contemplated and no teachings relating to the further disclosure added in the present CIP.

There accordingly exists an unsatisfied need for compositions for use in human or animal therapy or prophylaxis capable of making available B6 effectively and at a required rate, to compensate rapidly for or to pre-empt excessive cell depletion of B6 during a variety of pathological states to be dealt with more fully below.

GENERAL DESCRIPTION OF THE INVENTION

The present invention according to one aspect thereof provides a new method of treatment. According to a further aspect it provides new pharmaceutical or dietary compositions as well as combinations thereof with other drugs. According to yet another aspect the invention combines the method with certain diagnostic tests and provides the diagnostic means (more particularly in kit form) for carrying out those diagnostic tests.

The compositions according to the invention are generally supplied with appropriate instructions for carrying out the method (treatment or prophylaxis) as set out above. Such instructions may be oral but are preferably in written, printed or pictorial form, e.g. included in or applied to a package containing the compositions. Packages may take the form of dispensors, designed to prescribe to the patient a particular dosage regimen.

The present invention is based on the surprising finding that substantially improved and more rapid alleviation of B6 deficiency can be attained by administering to the patient an effective amount of a pharmaceutical or dietary composition, comprising as an active ingredient pyridoxal (PL) itself or a precursor of pyridoxal which in vivo, once it has entered the bloodstream, is rapidly converted into pyridoxal without the intervention of oxidase or oxygen, optionally with a stabiliser or antioxidant and/or a potentiator for the pyridoxal. Preferably the precursor of pyridoxal is one which is also rapidly converted as aforesaid without the intervention of kinase.

Pharmaceutical compositions comprising vitamin B6 for that purpose in the form of PL or said precursor have not been proposed or been available previously. In fact, there has been a distinct prejudice in the art against the administration of B6 in any form other than that of PN. That prejudice was based not only on cost but also on the relative stability and long shelf-life of PN. In vitro PL is far less stable. The art took no or insufficient congnisance of the fact that PN has an extremely short half-life in blood in vivo, that it is readily excreted and/or converted into physiologically unavailable compounds, and that PN must pass through a chain of biochemical reactions before it can enter the cells and finally end up there as required in the form of active vitamin B6, i.e. pyridoxal phosphate (PLP) and that this chain of reactions can be compromised at various stages, in different clinical situations.

Various facts are known, mostly in isolation, concerning B6, its occurrence and biochemistry. However, this knowledge has not been properly correlated, nor could the conclusions be drawn on which the present invention is based.

The present invention is based on the applicant's own, new experimental findings, including the pharmaookinetics of B6 vitamers in humans, a new interpretation of aspects of the biochemistry of B6 made possible by these experimental findings, as well as new concepts based on the results of our experiments throwing new light on various biochemical observations which previously were not understood or correlated. This has been made possible by our development for the first time of a practical method of determining PL in body fluids in the clinical situation.

The method according to the invention is applied to a variety of types of clinical situations, all involving the said depressed or inadequate intra cellular PLP levels, however, the following description will show that many, if not most clinical or pathological conditions fall into two or more of those types.

One type of such situations comprises conditions involving depressed cell oxygenation, depressed oxidase activity and/or depressed kinase activity. Depressed cell oxygenation (socalled anaerobic condition) is a common feature of many serious diseases. Depressed oxidase activity can be chemically induced by diseases or drugs or can be due to an enzymatic cellular defect.

A specific type of situation, e.g. physiologically and/or drug induced, involves also chemical pyridoxal phosphate depletion.

In a further type of situation the invention is applied to the treatment or prophylaxis of a condition involving inadequate or depressed intracellular pyridoxal phosphate, caused or enhanced by a drug or toxin or other chemical substance acting as an antagonist of vitamin B6 or causing an increased demand for vitamin B6. A specific such situation common to many forms of serious illness involves elevated blood biogenic polyamine levels. These may be derived from cell death in the patient or from microbial cells.

A major class of situations to which the invention is applied falls into the broad category of physiological shock as will be more fully explained. Myocardial infarction is for that purpose to be considered a severe form of physiological shock, although it also falls into other categories, e.g. anaerobic cell conditions and cell death (with release of biogenic polyamines which severely compromise intracellular PLP levels).

The invention is also applied to conditions involving the release of microbial toxins which on the one hand may induce physiological shock and on the other hand directly chemically interfere with the PN-PNP pathway.

The invention may be applied to domestic or wild animals in the context of animal capture sedation or transportation.

A further wide class to which the invention is to be applied involves depressed or absent enzymatic activity impairing said pathway, caused by an inherent cellular defect. This includes treatment of a patient suffering from a genetic lack of oxidase or genetic oxidase polymorphism.

It also includes the treatment of a condition wherein the depressed or absent enzymatic activity is caused by cellular immaturity. This in turn includes the treatment of infants suffering from intracellular pyridoxal phosphate insufficiency, in particular the treatment of premature infants.

A particular group of situations involves the treatment of a condition involving a depressed level of enzymatically mature or intact erythrocytes and/or lack of haemoglobin, e.g. as may occur in anemia or in a patient suffering from a microbial disease involving destruction of erythrocytes. Such disease usually in addition causes the release of toxins or biogenic polyamines.

A very special group of situations of chemically induced intracellular PLP depletion or insufficiency is induced by estrogen—i.e. either physiologically or pharmaceutically induced elevated estrogen levels.

The invention also provides that the disturbance of the pathway is measured and the effective amount of composition is administered in accordance with the degree of disturbance measured. e.g. by measuring the oxidase activity in a cell sample.

In a specific embodiment the oxidase activity is measured in erythrocytes by haemolysing under standardised conditions a sample of erythrocytes to prepare haemolysate, extracting the haemolysate with an organic solvent, after chemical denaturing of haemoglobin clarifying the resulting extract, dissolving the extract in buffer at a pH purging from 7 to 8, adding a known amount of pyridoxamine or the phophate thereof as a substrate and detecting the ammonia released by the action of the oxidase on the substrate under standardised conditions as a measure of the oxidase content. For that purpose the invention provides a new diagnostic kit.

Alternatively the disturbance is measured by determining the enzyme glutamate-pyruvate-transaminase and/or glutamate-oxaloacetate transaminase (GDT) activity in red blood cells.

According to the invention the pyridoxal or precursor is administered at a daily dosage rate, calculated on the basis of pyridoxal of 0.03 to 4.3 mg/kg bodyweight intravenously, or 0.04 to 5.7 mg/kg bodyweight intramuscularly or 0.04 to 7.2 mg/kg bodyweight subcutaneously, or 0.03 to 7.2 mg/kg bodyweight orally. Compositions according to the invention are formulated accordingly. Preferably the dosage rate is 0.07 to 2.2 mg/kg intravenously or 0.07 to 2.9 mg/kg intramuscularly or subcutaneously or 0.07 to 3.6 mg/kg orally.

In addition zinc and/or magnesium may be provided as a potentiator for pyridoxal at a dosage rate of 0.05 to 0.9 mg/kg/day of zinc and 0.5 to 10 mg/kg/day of magnesium. Particularly, where anerobic intracellular conditions are to be treated, glutamate may serve as a potentiator, e.g. at a dosage rate of 0.04 to 20 mg/kg/day.

For reasons still to be explained below the invention produces maximum benefits if the composition according to the invention is provided as an infusion or in another sustained, continuous release galenic form.

In the embodiments for the treatment of immature infants the dosage rate calculated as pyridoxal is 0.01 to 1.0 mg/kg bodyweight per day intravenously, 0.017 to 2.0 mg/kg bodyweight per day intramuscularly or subcutaneously or 0.008 to 1.0 mg/kg bodyweight per day orally. Here as well the composition may be administered as an infusion. In addition or in the alternative the composition is added in the form of a nutritional supplement in dosage units to a feed formulation or the composition is itself an infant formulation containing the said pyridoxal or precursor in the required concentration for oral administration.

The aforegoing teachings applicable to the method apply analogously to the galenic forms and dosage units in which compositions according to the invention are presented.

In dietary compositions the pyridoxal or precursor becomes partly absorbed in the components of the diet resulting in a degree of slow, sustained continuous release effect. If the composition is presented as an infusion, that effect results from the manner of administration. Galenic forms of presentation are preferably galenically formulated for infusion or for another form of sustained, continuous release of pyridoxal or said precursor to the patient. Because of the mechanisms involved in the use of the invention, it is particularly important for maximum beneficial effects that the relatively low concentrations of pyridoxal are made available to the body continuously over a prolonged period, as evenly as possible.

According to certain embodiments, the composition comprises PL or a physiologically compatible acid addition salt or complex of PL which in vivo rapidly releases PL, or a mixture composed of two or more of these as the only source or sources of vitamin B6.

To protect against aerial oxidation, the composition (whether provided in solution form or as a solid, e.g. a Powder) preferably contains an antioxidant, for example ascorbic acid (or a physiologically compatible salt thereof), the latter, for example, in a concentration of from 1 to 5000 mg per liter, preferably 50–500 mg per liter, e.g. 100 mg per liter, the concentrations given referring to a composition in the form of a parenteral solution, e.g. an infusiuon solution or to the required antioxidant content of a composition provided in the form of a powder to yield the stated concentration in an infusion solution, prepared therefrom. Even near the lower limit, ascorbic acid is effective as an antioxidant. However, in the higher concentrations, ascorbic acid also becomes effective physiologically as a source of vitamin C which is often desirable, e.g. in infusion solutions. An alternative or additional antioxidant may be sodium metabisulphite or any other compatible biological anti-oxidant.

Although PL is readily resorbed when administered for example per os, preferred embodiments, particularly for emergency use, are in a form adapted for or readily adaptable for parenteral administration, preferably intravenous administration and in particular in a form adapted for or readily adapted for intravenous infusion. The latter embodiments may contain the conventional ingredients of an infusion solution, for example electrolytes, glucose and/or conventional extenders, excipients and the like. Since B6 in the form of PL in solution has a limited shelf-life, the composition may alternatively be provided in the form of a dry powder, preferably vacuum-packed in dark-coloured ampoules, the dry powder containing all the required additives to permit immediate use of the composition as an infusion solution after dissolution in, and suitable dilution to the required concentration with, sterile water. Alternatively, the powdered form of the pharmaceutical composition may be adapted such that it may be dissolved in any other standard infusion solution used under these circumstances.

As a further alternative the composition in powder form may be separately made up with sterile water and mixed with any other standard infusion solution before use; or said solution of the composition may be made up separately and administered together with a standard infusion solution after mixing in the feed tube of the infusion apparatus according to known art.

Preferred embodiments of the composition comprise as a further ingredient or ingredients one or more of the substances: glutamate, riboflavine, and physiologically compatible salts of zinc and magnesium.

Riboflavine, zinc ions and magnesium ions are co-factors in the enzymatic conversion of PN into PL, and zinc ions and magnesium ions are also co-factors in the phosphylation of the vitamers PN and PL. Therefore these substances augment the conversion of PN when administered as part of the composition or separately, e.g. with the diet, even in patients suffering from reduced liver function to make more PL available to the body, and thereby augment the administration of PL in accordance with the present invention. Furthermore, as explained later in this specification, efficient glycolysis during ischaemia, e.g. in a coronary heart patient, is not only dependent on functionally available intracellular PLP, the phosphorylated form of PL (which according to the invention is supplemented by intravenous administration of a PL-containing infusion solution), but the action of the PLP during the critical period following a myocardial infarction (MI) incident is assisted by the provision of supplementary glutamate. Similar benefits arise from glutamate supplementation in other cells.

Sometimes it is desirable to include in the composition in addition pyridoxine or pyridoxine phosphate or a pharmaceutically acceptable complex or acid addition salt thereof in an amount not exceeding that of the pyridoxal or its precursor, and in such cases in particular it is preferred to include riboflavin as a cofactor or potentiator for pyridoxine in an amount adapted to provide an effective dosage rate of 0.05 to 0.2 mg/kg/day, for example. This applies particularly to infant feed formulae and supplements or feed additives, where it is desirable to stimulate the enzyme system of the immature cells so as to develop its normal ability to convert PN into intracellular PLP.

Infant feed formulae or additives or nutritional supplements for such formulae will generally comprise pyridoxal or said precursor in such concentration that the daily intake will be in the range 0.008 to 1.0 mg/kg bodyweight of pyridoxal. More particularly the said concentration is such that the daily intake of pyridoxal will be in the range 0.06 to 0.16 mg/kg. In the case of an additive or nutritional supplement, this is preferably in dosage units containing pyridoxal or said precursor in such concentration that the daily intake is distributed over from 1 to 6 dosage units. For example, such composition is in the form of solid dosage units formulated for a daily intake equivalent to from 0.008 to 0.8 mg/kg bodyweight pyridoxal or pyridoxamine or from 0.013 to 1.2 mg/kg bodyweight of pyridoxal phosphate or pyridoxamine phosphate, or a mixture of the aforegoing, wherein the said intake is divided pro rata. The phosphates are used in such somewhat higher concentration to allow for losses during the conversion into PL. The preferred infant formula or nutritional supplement or additive in addition contains pyridoxine or a complex or acid addition salt of pyridoxine in a concentration adapted to provide a daily intake of pyridoxine of 0.007 to 1.0 mg/kg bodyweight and preferably in addition contains riboflavin in a concentration adapted to provide a daily intake of 0.05 to 0.2 mg/kg bodyweight.

Of particular importance in the context of intracellular enzymatic insufficiencies involving the PN-PLP pathway are compositions according to the invention for use in the treatment or management of a condition involving microbial infection causing erythrocyte destruction, e.g. for use in the treatment or management of malaria, bartonelosis, Rift Valley fever, corridor disease or biliary fever. These may be used or formulated in combination with a drug for combating the microbial infection in a common package or in a common dosage form.

It will be understood from the principles underlying the present invention, that compositions in accordance with the invention may be provided with great advantage in the form of a blood supplement or substitute or blood transfusion composition or an additive for addition to any of the aforegoing.

The invention specifically provides compositions as aforedefined for use in combination with an estrogen administration regimen or to counteract effects of elevated biogenic estrogen levels. These are preferably combined with an estrogen composition in a common package.

According to one embodiment the estrogen and the pyridoxal or said precursor are combined in a single dosage form. According to an alternative embodiment the estrogen on the one hand and the pyridoxal or said precursor are wholly or in part provided each in separate dosage forms but in a common package. Advantageously the dosage form or dosage forms are arranged in the package in a pattern prescribing a dosage regimen over a treatment period equivalent to one or a plurality of menstrual cycles or selected portion(s) thereof.

Such pattern may moreover prescribe a dosage regimen adapted to the menstrual cycle. In other words with differences in respect of dosage rate or rates for different portions of the menstrual cycle, either as regards the pyridoxal or precursor, or as regards the hormonal component(s) of the regimen.

Likewise compositions according to the invention may comprise the pyridoxal or precursor thereof, in combination with a drug, acting as an antagonist for vitamin B6 or causing an increased demand for vitamin B6 as a further active ingredient in a common dosage form or in separate dosage forms in the same package.

Thus the invention contemplates that said separate dosage forms are packaged side by side in pairs for combined administration. Specific examples will be dealt with further below. One specific class of such drugs, i.e. xanthine bronchodilators, is dealt with extensively in U.S. Ser. No. 07/153,973 (and corresponding European patent application 88 90 1822.2) Publ. No. 302097) and in the copending CIP thereof, U.S. Ser. No. 07/395033. The relevant contents of those applications, by reference thereto are to be considered part of the present disclosure.

The combination composition and combination package described in the preceding paragraph may comprise a succession of combinations in different ratios or quantities of pyridoxal or precursor on the one hand and said further active ingredient packaged in a package prescribing a dosage regimen over a prolonged period.

Analogously the invention contemplates a composition according to the invention comprising said pyridoxal or precursor thereof, in combination with another drug for the treatment or prophylaxis of a disease or pathological condition, one of the symptoms of which is an inadequate or depressed intracellular pyridoxal phosphate level, as a further active ingredient in a common dosage form or in separate dosage forms in the same package. Such further ingredient may or may not be itself one which acts as an antagonist for vitamin B6 or causes an increased demand for vitamin B6. In such embodiments as well the aforegoing teachings pertaining to separate dosage forms in a common package and dosage regimens prescribed by the package apply in analogous manner.

DETAILED EXPLANATION OF INVENTION AND DESCRIPTION OF PREFERRED EMBODIMENTS

The following explanations and examples are to be read in conjunction with the more general description further above and with the claims to obtain a full disclosure of the present invention.

The invention teaches a new use in therapy and prophylaxis of pyridoxal or certain precursors thereof.

The preferred compound to be used in accordance with the invention is pyridoxal itself, because that is the compound which can be utilised directly to meet the deficiency. It is the only form capable of entering directly into tissue and other B6-deprived cells, in order to be converted there directly into peridoxal phosphate (PLP) (the only active form of B6) by the action of kinase (and its co-factor adenosine triphosphate—ATP).

PLP can be administered, according to the invention, but is less preferred, because in the gut it must first be hydrolysed to PL before absorption can occur, and also in the plasma it must first undergo hydrolysis to PL before it can enter into the cells. Although the enzymes required for such hydrolysis are usually available in the gut and in plasma, the hydrolysis is not instantaneous and delays the availability of the PL. Moreover, these enzymes can be inhibited by drugs in certain pathological conditions. On the other hand and because of these considerations, PLP can be utilised as an effective slow release form of PL, e.g. in dietary or pharmaceutical compositions for oral use in cases, where these pathological conditions do not arise.

Pyridoxamine (PM) and its phosphate (PMP) can also be used. Pyridoxamine can also enter the cell directly, in contrast to PMP, which like PLP must first be hydrolysed and in that respect suffers from the same disadvantages. In spite of the above reasons which usually render PLP and PMP less preferred, there can be circumstances which render the inherent sustained or delayed release of PL and PM by those substances desirable.

The enzymes which are needed to convert PM into PL are normally readily available, both inside and outside of the cells, so that the reason why PL is more preferred is mainly the potential delay caused by this reaction. A possible advantage of PM is its greater stability. However, the stability of PL in pharmaceutical formulations can be enhanced satisfactorily by antioxidants such as ascorbic acid (vit C) and/or sodium metabisulphite.

Pyridoxal (as well as PM) can be employed in the form of pharmaceutically acceptable acid addition salts (e.g. the hydrochlorides) or of complexes capable of the rapid release of PL and/or PM in vivo. The following, in accordance with the invention, are examples of complexes and derivatives of pyridoxal capable of releasing pyridoxal readily in vivo, and are therefore ordinarily suitable for use instead of pyridoxal itself and in preference to pyridoxine:

I) Addition salts of PL and pharmaceutically acceptable acids, for example: HCl (preferred), $H_2SO_4$, $H_3PO_4$, certain amino acids, e.g. glutamine, asparagine, glutamic acid;

II) Acetals, resulting from the addition of an alcohol to the aldehyde group of PL. A typical example is pyridoxal monoethyl acetal hydrochloride.

III) Condensation products arising from the reaction of the aldehyde group with an amine, leading to the formation of amino alcohols or Schiff bases:

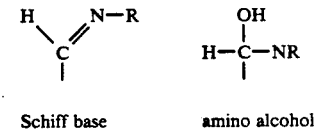

Schiff base          amino alcohol

The amine is preferably a biogenic or biological amine having desirable biological properties, e.g.

(1) Amino acids (e.g. L-lysine, L-arginine, glycine)

(2) Pyridoxamine (PM); both PL and PLP will react with PM or PMP to form a Schiff base derivative,

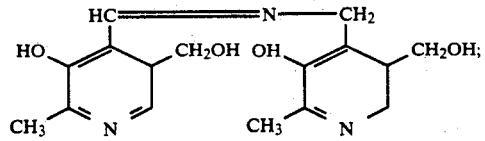

this Schiff base is a preferred derivative for the purposes of the present invention. In vivo it is a source of both PL and PM.

(3) Taurine (4) Suitable diamines, e.g. ethylenediamine; ethylenediamine reacts with PL to form a compound which in turn forms a sparingly soluble magnesium complex which may be used according to the invention as a source of both PL and Mg.

The invention is based on the realisation that in the aforesaid conditions, associated with often severely reduced blood and cellular B6 depletion, the administration of PL is substantially more effective than PN to counteract such depletion, being effective even in patients who do not respond to conventional administration of PN. A direct inverse correlation exists between the degree of B6 depletion of critically ill patients and their chances of survival. Medical and surgical complication such as shock, hepatic failure, infection and sepsis, wound dehiscence, incisional hernia, aminoglycoside induced renal failure and impaired skin and mucosal regeneration, hematopoiesis, hormone production and wound repair; multi-organ dysfunction, respiratory distress and also severe depression are substantially more frequent in B6 deficient patients. These conditions are, inter alia, causally related to impairment of immune function, collagen and elastin cross-linking and polyamine synthesis and accumulation. Those patients who end up with a plasma content of phosphorylated PL (i.e. PLP) of 20 nM or greater usually survived, and those with a final PLP content of 10 nM or less usually did not. Patients who were destined to die had a poor response to conventional B6 supplementation: their increment in plasma PLP with hyperalimentation and additional PN was generally less than 10 nM and occasionally less than 1 nM, even with 200mg/day of PN. With hindsight the probable reasons why the administration of PL can surprisingly overcome or mitigate this problem will be explained further below in this specification. However, the correctness or otherwise of any explanations given or mechanisms postulated is not to limit the scope of the invention or to be relevant to the inventive merits of the invention as claimed.

As briefly shown in the general description of the invention, the inventive use of pyridoxal or its precursors for the management of depressed or inadequate intracellular PLP levels and increased vitamin B6 demand is broadly concerned with conditions wherein the PN-PLP pathway is disturbed or insufficient. This may be due to an intracellular oxidase and/or oxygen deficiency. It often also involves a kinase deficiency.

These situations of enzymatic disturbance or insufficiency may broadly be divided into two broad categories. The first category comprises those where the disturbance or insufficiency is due to chemical factors (internal or externally introduced) which comprise the relevant enzymes and/or inactivate or remove intracellular PLP. The second category has as its common cause an inherent intracellular enzyme deficiency or defect. Some situations belong to both categories. Specific examples of these categories will be dealt with below.

Chemical factors include those in physiological shock. Physiological shock is generally characterised by hypotension, exhaustion, pale cold moist skin, collapse of surface veins and reduced urine production.

Physiological shock may be defined as a state in which there is widespread and serious reduction of tissue perfusion which, if prolonged, leads to generalised impairment of cellular function. An important reason for the impaired cellular function is the reduced supply of essential nutrients (vitamins, glucose, etc.) to the cells as a result of the reduced tissue perfusion, which may ultimately lead to cell death and the liberation of cellular contents including B6 antagonists such as amines and polyamines such as spermine and spermidine into the surrounding body fluids, which in turn affect the vital B6 status of the patient, inter alia due to the reaction of B6 with polyamines and to the enzyme inhibitory properties of polyamines.

The role of intracellular PLP in physiological shock is complex: Firstly the heart delivers too little blood to maintain effective tissue and organ perfusion (ischemia). This leads to reduced oxygen supply and reduced erobic metabolism and an increased demand for anerobic metabolism. PLP (with glutamate as a cofactor) plays an important role in promoting and maintaining anerobic metabolism in the cell. The primary effect is an increased demand for intracellular PLP, followed by intracellular PLP depletion, which cannot be met adequately along the normal PN-PLP pathway. This is aggravated because the various symptoms of severe shock cumulatively compromise the PA-PLP pathway: impaired liver perfusion required for the activation of PN becomes seriously impaired. The aforesaid biogenic B6 antagonists not only inactivate existing PLP and remove PL, but also inhibit oxidase and kinase needed in the said pathway.

The present invention supplies this need by the administration of pyridoxal (PL) or the said precursors or a mixture of both. This not only accelerates the availability of PLP in the cells but also bypasses the bottlenecks created by the impaired PN-PLP pathway. That latter bottleneck cannot be overcome by the administration of increased dosages of pyridoxine. On the contrary, for the reasons explained further below such increased dosages may aggravate the situation inter alia by intracellular competition by PN and PNP for available enzymes. Such excessive dosages result in side effects with symptoms which paradoxically are similar to those of a vitamin B6 shortage.

There are many different causes and types of shock, including hypovolaemia, internal sequestration, cardiogenic shock, trauma, surgery, loss of blood, obstruction of blood flow, neuropathic shock, infection, anaphylaxis, anoxia, toxaemia and others, including the terminal stages of many diseases, all resulting in B6 depletion in plasma and cells, which is physiologically harmful.

The basic common physiological defect induced by shock is reduced venous return and decreased cardiac output, which eventually lead to reduced tissue perfusion and ultimately cellular damage and death.

A complex form of shock may result from infections, which is often associated with the release of endotoxin, the lipopolysaccharide moiety of bacterial cell walls. In addition, many of the drugs used for the treatment of infections cause a further lowering of the B6 status of the patient, thus inhibiting the cellular energy producing mechanisms, and therefore compounding the clinical consequences.

Myocardial disease leading to MI is to be considered a particularly severe and often fatal physiological shock situation wherein cells, in this particular instance myocardial cells, enter into a physiological shock condition and undergo a depletion, and a resultant physiologically harmful shortage of B6, in particular PLP and PL. Such depletion is due to increased cellular demand and to the action of liberated polyamines (PA) and other amines known to be B6 antagonists. This is reflected in the lowered serum B6 levels seen in coronary patients immediately after the incident. According to the invention the harmful effect of physiological shock on the cells—i.e. infarction—is counteracted, mitigated, prevented or limited by the administration of PL to meet this shortage.

MI and other diseases involving shock may eventually enter a terminal phase characterised by the multi-organ failure syndrome, often due to the synergistic effect of the polyamines spermine and spermidine acting in unison with iatrogenically administered B6 antagonistic drugs. This is due to complex formation with B6 vitamers and/or enzyme inhibition. In the case of spermine, spermidine and many B6 antagonistic drugs, these complexes involve the irreversible formation of aldamine rings and permanent loss of B6 activity.

In addition, the inventor has now demonstrated the existence of two specific PLP-phosphatases in red blood cells (only one of which occurs in serum) which are functionally different from the urual alkaline phosphatase and which are inhibited by unidentified compounds in the serum of seriously ill patients and also by spermine and spermidine. In this manner the hydrolysis of PLP to PL (the physiological mechanism by means of which vital serum PL levels are maintained is compromised in the seriously ill patient.

The invention teaches the administration of pyridoxal and its precursors in combination with drugs which are antagonistic to vitamin B6, thereby to provide relief from or prophylaxis against intracellular PLP depletion resulting from such drugs.

Drugs which are antagonistic to B6, and the toxicity of which aggravates the B6 depletion in patients due to spermine and other amines and polyamines released by dying cells (whereby the toxicities are synergistically enhanced), include aminoglycosides (e.g. gentamycin), cycloserine; xanthine bronchodilators, e.g. theophylline-type drugs (including theophylline itself and in particular aminophylline); 1-dopa, dopamine, penicillamine, digoxin, oral contraceptives, anti-depressants (iproniazid, niamic, isocarbazid, malamid, marpian), amphetamines, MAO inhibitors (e.g. phenelzine), amitryptylline; anti-TB, drugs e.g. isonicotinyl hydrazide (INH): azaribine (psoriasis), anti-hypertensives (hydralazine); anti-cancer drugs (e.g. proconbazine); cycloserine; amphetamines; carbamazepin; diphenyl hydantoin.

The highest toxic synergism with biogenic polyamines results from drugs carrying 1,2 or 1,3 diamine moieties (e.g. —$CHNH_2$—$CHNH_2$—), e.g. gentamycin, histamine, resulting in the irreversible formation of aldamine rings.

Some of these drugs are normally given to patients suffering from severe diseases. However, although the drug may combat effectively the disease itself, there is an enhanced toxic effect and B6-lowering effect when given to severely ill patients with elevated polyamine levels. Death may result. As an example: gentamycin is routinely given to patents with severe gramnegative infections. The terminal phase is characterised by the multi-organ failure syndrome, often due to the synergistic effect of the polyamines spermine and spermidine acting in unison with iatrogenically administered B6 antagonistic drugs, such as gentamycin.

The administration of PN is often ineffective to counteract the B6 depletion in these situations. The present invention teaches to administer PL instead, preferably intravenously, to provide a rapid supply of active B6 in plasma and cells.

It is believed that some of the superiority of PL over other B6 vitamers, in Particular PN, is based on the combination of principles and mechanisms postulated in what follows, which appears to fit biochemical and clinical observations:

PLP, i.e. the phosphorylated form of PL, is the active form of B6 inside cells as well as in the blood plasma. However, none of the phosphorylated B6 vitamers (PLP, PMP, PNP) is able to cross biological membranes (except those of the healthy liver), so that the intracellular levels of essential PLP depend upon the intracellular availability of PL or PN, which are the main precursors of PLP and which readily cross cell membranes.

PN as used in conventional B6 preparations must pass through a series of enzymatic reactions before it becomes available inside the various cells in its active form, PLP. Although PN, being non-phosphorylated, is capable of crossing biological membranes and entering into cells, it is useless inside the cell unless firstly it is converted (either before or after entering the cell) by the kinase enzyme into PNP, and secondly (and this must happen inside the respective cell) into PLP, by the action of the oxidase enzyme.

PL kinase is widely distributed in the body, including the myocardium. In contrast, the PN(PNP) oxidase system is confined to a few tissues and is either absent or present in very low concentrations in the heart and most other cells. It is present in relative abundance only in the liver, and even there only if the liver function is intact. This leads to the important conclusion that in tissues other than the healthy liver there is a long lag period for the synthesis of PLP after parenteral injection of PN, since conversion of PN into PLP takes place essentially only in the liver. If the liver function is impaired or absent (depressed liver function or liver perfusion), as may often happen in severely ill patients, particularly when multiple organ disfunction has set in, the conversion of PN into PL and PLP is compromised and PN-supplementation is rendered ineffective. It is a unique property of healthy liver tissue (as contrasted with other cells) that it is able to release to the plasma PLP bound to albumin.

Moreover, the plasma half-life of PN in man is only about 12 minutes. The administration of high doses of PN under these conditions is in fact counterproductive. The initial step of PN activation inside cells may either be kinase induced phosphorylation to PNP (followed by oxidase catalysed oxidation to PLP) or initially oxidase induced oxidation of PN to PL (followed by kinase catalysed phosphoylation to PLP). Both PN and PL therefore compete for the same kinase enzyme, and in the presence of excess PN, the phosphorylation of PL is compromised. In addition it would appear that PN may inhibit the entry of PL into cells. PNP, once formed in any cells other than liver tissue, is metabolically trapped and is no longer available for conversion into PLP.

Administration of PLP is also less rapidly effective than PL. PLP must first be de-phosphorylated in the plasma (by the newly discovered PLP-specific phosphatases referred to above) before it can enter the cells where B6 is needed. This involves a delay and presupposes the availability of the necessary enzymes (phosphatase) and the absence of factors inhibiting these enzymes. Moreover, PLP is substantially more prone to becoming protein (albumin) bound than PL.

This confirms the inventive concept that administration of PL (or PM) is the universally effective emergency procedure for restoring cellular B6 activity in serious disease conditions, whether or not this is accompanied by concomitant therapy with drugs that may be B6 antagonistic.

The clinical significance of PL was not previously recognized, inter alia because it was not appreciated that biological utilisation and activation of PN may be severely compromised in many acute disease condition, or that administration of PN under these circumstances may in fact be counterproductive in that high levels of PN not only suppress cellular PL uptake, but high intracellular PN levels compete with available PL for the common kinase enzyme system used to phosphorylate both PN and PL intracellularly. The PLP plasma levels cannot be restored to normal in some critically ill patients even by giving large doses of PN, since those patients are no longer in a position to benefit metabolically from such treatment.

The invention teaches that in treating a coronary patient, in addition to the usual measures (streptokinase, beta-blockers, coronary vasodilators, etc.), the immediate intravenous administration (preferably by way of infusions) of a solution containing PL and electrolytes (either as such or in combination with glucose and other necessary cc-factors, including riboflavine, zinc ions and magnesium ions) is an important and essential emergency step in limiting infarct size. Also, it is beneficial to administer glutamate.

Coronary patients have significantly depressed PLP levels during the 24 h period immediately following the MI incident, inter alia due to increased cellular demand during this period for PLP in the myocardium. This pathophysiological condition is considered to be due to oxygen deprivation of at least some of the tissues involved and to involve the following mechanisms:

A muscle, e.g. the heart muscle is able to utilise different substrates as energy sources, including fatty acids, lactate and glucose. In the well-perfused and oxygenated heart, fatty acids are the prime source of energy, taking precendence over the process of glycolysis as energy source. However, in the absence of adequate supplies of oxygen following local myocardial ischaemia, energy production becomes dependent on the less efficient but rapidly mobilised process of glycolysis. The enzyme glycogen phosphorylase, which catalyses the hydrolysis of muscle glycogen to yield glucose required as energy source in the process of glycolysis, utilises PLP as co-enzyme. Efficient and rapid glycolysis therefore depends on the availability of adequate intracellular supplies of PLP, and this is achieved by infusion of PL.

During glycolysis the oxidation of glyceraldehyde-3-phosphate to glycerate 1,3-diphosphate produces NADH (reduced form of nicotinamide adenine dinucleotide), which eventually leads to cellular depletion of NAD (nicotinamide adenine dinucleotide) unless the NADH produced is re-oxidised. Glucose oxidation via the process of glycolysis can therefore only continue if the NADH produced is removed in such a manner that NAD is regenerated. Since NADH is an inhibitor of the enzyme glyceraldehyde-3-phosphate dehydrogenase, feedback control by product ihhibition plays a role in restricting glycolysis in ischaemic cells with impaired ability to re-oxidise NADH.

Normally in the well-oxygenated cell the electron transport chain situated in the mitochondria oxidatively removes the accumulated NADH. However, the mitochondrial membrane is impermeable to NADH, so that NADH produced in the cytosol cannot be removed in this manner. This problem can be circumvented in the myocardial cell by means of the malate-aspartate shuttle, which is capable of indirectly transporting electrons from NADH across the mitochondrial membrane, thus reoxidising NADH to NAD. NADH in the cytoplasm is oxidised to NAD by donating electrons to reduce oxaloacetate to malate, the latter being readily transported across the mitochondrial membrane. Inside the mitochondrion, malate is re-oxidised to oxalo-acetate, with simultaneous reduction of NAD. The mitochondrial membrane is, however, impermeable to oxaloacetate, which would therefore accumulate unless effectively removed. This is achieved by means of a further PLP dependent transamination of oxaloacetate to aspartate, the amino group in this exchange reaction being supplied by glutamate, a substance capable of freely crossing the mitochondrial membrane in either direction. The mitochondrial membrane is also freely permeable to the aspartate produced intra-mitochondrially in this manner, and it is therefore transported to the cytoplasm, where it is subsequently transaminated to oxaloacetate in a reaction which is again PLP dependent. Thus the cytoplasmic removal of NADH and confirmed effective glycolysis is dependent on the availability of adequate intracellular supplies of PLP, supplemented according to the invention by infusion of PL or precursor thereof.

The aforegoing furthermore explains why, according to the invention, supplementation with glutamate is also of importance, since the malate-aspartate shuttle depends on the presence of glutamate in the ischaemic heart muscle cell (and indeed in other ischaemic cells as well). However, by supplying both PL and glutamate, the overall effect is more than would be expected from simple summation of the effects.

The foregoing also supports the teaching that PL administration, for example by means of a suitable infusion, may be used to reduce and control elevated polyamine (PA) levels in the blood associated with certain renal and other conditions in order to eliminate, prevent or pre-empt PA toxicity.

Yet another application of PL therapy or prophylaxis is when used as a means to increase the patient's B6 status before or even during major surgery or with any other critical condition, to improve the prognosis and outcome, especially in the debilitated, the elderly and those requiring massive procedures.

Since in many conditions, actual or incipient B6 deficiency (for example caused by increased PA levels arising from the condition or caused by medicaments used in the treatment) may not be suspected, the invention proposes the prophylactic inclusion of B6, partly or wholly in the form of PL, in essentially all infusion solutions and solutions used for parenteral administration. Furthermore, the inclusion of PL in infusion solutions may in general be used to decrease or control the "amine load" in the very ill patient.

No adverse effects of PL administration in experimental animals or humans are known.

The category of chemical factors which cause depressed or inadequate intracellular pyridoxal phosphate levels and an increased pyridoxal phosphate demand which is to be met, in accordance with the invention by an administration of pyridoxal or said precursor is not confined to the aforesaid serious and often life-threatening diseases. Thus the invention also provides an effective method and pharmaceutical compositions for the treatment or prophylaxis of conditions associated with biogenically or pharmacologically induced elevated estrogen levels causing an increased intracellular demand for or depletion of pyridoxal (phosphate).

It is known that biogenically or pharmacologically induced elevated estrogen levels cause an increased intracellular demand for or depletion of pyridoxal phosphate and a number of side effects, notably mood changes and depression. This is caused by an abnormal tryptophane (Tryp) metabolism as evidenced by an increased activity of the Kynurenine pathway as (partly) reflected in the following reaction scheme

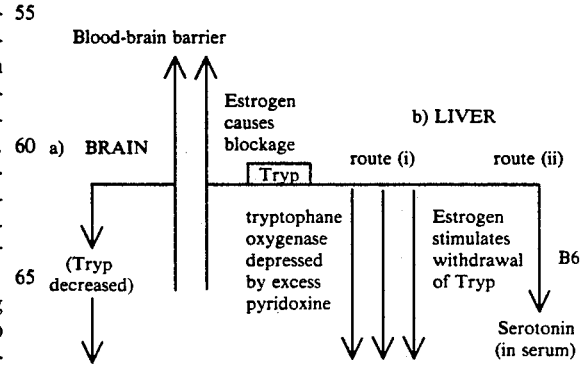

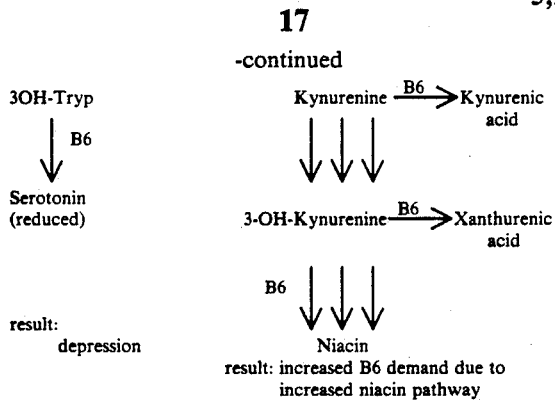

As shown in the reaction scheme, tryptophane is metabolized along two pathways:

a) in the brain: tryptophane, after passing trough the blood-brain barrier, is metabolised by a series of vitamin B6 dependent enzymatic reactions to serotonin. A shortable of serotonin in the brain causes depression.

b) in the liver:
  (i) tryptophane is converted by tryptophane oxygenase and in a variety of successive steps into niacin. The final step is vitamin B6 dependent but susceptible to Vitamin B6 deficiency. Two side reactions leading to kynurenic acid and xanthurenic acid are likewise promoted by vitamin B6, but these reactions are less suscptible to vitamin B6 deficiency than the former.
  (ii) Some tryptophane is converted in the liver along a third vitamin B6-dependent route into serotonin which enters the bloodstream. This serotonin cannot enter the brain due to the blood brain tarrier. This third route is of secondary importance in the present context.

Elevated estrogen levels have two major effects on these pathways:

firstly estrogen stimulates the oxygenase activity in pathway (b)(i), thereby greatly increasing the withdrawal of tryptophane via that pathway, leading to a substantially increased vitamin B6 demand because of the many reactions there which require vitamin B6 in its active form, i.e. pyridoxal phosphate.

Pathway b(ii), leading to serotonin in the circulation, withdraws some of the remaining tryptophan, at a rate which may be somewhat reduced by the increased demand of pathway b(i) for tryptophan and vitamin B6.

Withdrawal of tryptophane along pathways (b)(i) and (ii) causes a substantial reduction of tryptophane available for pathway (a).

Estrogen and estrogen conjugates, hereinafter generally referred to as estrogen, furthermore cause a blockage of the blood-brain tarrier with respect to the entry of Tryptophane which further reduces the availability of tryptophane for pathway (a). Moreover, the depletion of vitamin B6, caused by the increased demand therefor along pathway (b), further compromises the vitamin B6-dependent reactions along pathway (a). The result of this is a depletion of serotonin in the brain which causes adverse symptoms i.a. in the form of mood changes, notably depression.

These adverse symptoms may be caused naturally, i.e. by physiologically induced elevated estrogen levels as may occur e.g. during the last week before menstruation, leading to the development of pre-menstrual tension syndrome (PMS). Known PMS symptoms, besides mood changes, include inter alia bloated feeling, swollen breasts, and disturbed electrolyte balance. Different symptoms may be present in different patients and usually disappear promptly at the beginning of menstrual flow.

Similar and further symptoms are known to accompany the therapeutic or prophylactic administration of estrogen-containing pharmaceutical compositions. Thus quite unexpectedly PMS symptoms may persist after the menopause or after the surgical removal of ovaries when such patients are given estrogen therapy (normally oral) for various reasons, including the retardation of osteoporosis. No doubt these symptoms are related to the aforesaid tryptophane pathways being distorted.

The same is observed with users of estrogen-containing contraceptives, usually in the form of oral contraceptives, particularly amongst longterm users of oral contraceptives. Besides the aforegoing, other symptoms include increased serum lipid levels, hypertension, impaired glucose tolerance and thromboembolism.

The long term use of OC is of particular clinical significance. Evidence exists that such effects may even be apparent in babies born to long term OC users as opposed to short term users (Fed. Proc. 1981, 40: 864)

It is now also well established that these side effects of estrogen, related to a distorted tryptophane metabolism, are also accompanied by a long term functional vitamin B6 deficiency. Less well known is the adverse effect on lipid metabolism. Long term OC usage leads to reduced HDL cholesterol levels as well as increased LDL levels. These unfavourable effects on lipid metabolism are less obvious in the low estrogen formulations although similar distortions of lipid profiles may be seen in some patients after prolonged use of OC.

Supplementation with pyridoxine has been recommended, pyridoxine being the only form in which vitamin B6 is commercially available to date for pharmaceutical purposes with the result that pyridoxine has become synonymous in medical circles with vitamin B6.

Oral administration of B6 (in the form of pyridoxine) has been repeatedly shown to normalise Tryp. metabolism and also the associated clinical symptoms such as mood change in OC users.

In view of the adverse effects associated with the long term use of OC, the potency of the estrogen component has now been reduced from 50 µg to 35 µg. The low estrogen OC formulations are now associated with fewer side effects. However, a daily intake of at least 5 mg of B6 is still recommended in OC users (see for example Goodman and Gillman "The pharmacological basis of therapeutics" 5th Ed. 1975). In accordance with authoritative, more recent publications that dosage rate is far too conservative. According to these the role of vitamin B6 in relation to the development of PMS is of considerable and welldocumented clinical significance. Many scientific publications have confirmed the usefulness of pyridoxine (as source of vitamin B6) in the management of PMS and in most of these studies relatively high bolus doses of pyridoxine have been used (e.g 200-400 mg daily) and have been shown to be necessary, because lower dosages are not or not sufficiently effective.

However, the employment of pyridoxine at such high bolus dosage levels has now been found to have its own disadvantages. On the one hand the need for an excess of pyridoxine arises from the fact that such excess is needed in order to meet the increased demand for vitamin B6 resulting from the increased tryptophane oxygenase activity which activates the tryptophane (b)(i) pathway described above, pyridoxal phosphate, derived from pyridoxine is needed inter alia in the brain for the tryptophane—serotonin pathway (a) to counteract the estrogen-induced shortfall of serotonin, and wherever else vitamin B6 depletion has been caused by estrogen. However, at such high dosage levels required for that effect pyridoxine itself produces side effects, which, paradoxically, are similar to some symptoms of a vitamin B6 shortage.

Surprisingly it has now been found that pyridoxal supplementation is far more effective. It counteracts the side effects of estrogen at much lower dosages, than the dosages needed for that purpose in prior art supplementation with pyridoxine, at the same time avoiding the drawbacks of high dosage pyridoxine administration. The much greater effectiveness of pyridoxal is particularly surprising because pyridoxal cannot have any effect on one of the mechanisms by which pyridoxine, was previously believed to be effective, i.e. the reduction of tryptophane oxidase activity in Pathway (b)(i). Whereas pyridoxine must generally be employed in dosages of 200 to 400 mg/day, pyridoxal is found to be effective at dosage rates as low as a few mg/day, particularly, when the treatment is applied over prolonged periods, preferably in excess of 6 months.

On the basis of the aforegoing the invention teaches a method carried out with compositions as aforesaid comprising pyridoxal or a precursors as defined applied to a condition wherein an intracellular PLP depletion or insufficiency is induced by estrogen. Such elevated estrogen levels may be physiologically or pharmacologically induced.

The new method and composition may be applied to the treatment or prophylaxis of pre-menstrual tension syndrome or conditions producing similar symptoms associated with the pharmaceutical administration of estrogen. For example the composition is administered as part of a regimen of administering estrogen in a contraceptive composition or in a hormonal supplement composition, e.g. wherein the estrogen is administered as an oral contraceptive or for the management of an estrogen deficiency. For example, the invention may be applied to cases wherein the estrogen is administered for the management of an estrogen deficiency resulting from defective ovaries or the removal of ovaries, menopausal or post-menopausal conditions or in the treatment or prophylaxis of osteoporosis.

For those purposes the pyridoxal or its precursor is administered at a dosage rate in the range of 2 mg to 50 mg per day per adult patient calculated as pyridoxal, applied over a period equivalent to at least one menstrual cycle or a selected portion or portions thereof. Preferably the dosage rate is in the range of 5 mg to 25 mg per day and is applied over a period equivalent to at least 2 menstrual cycles or selected portions thereof.

According to some embodiments the relationships in terms of time and dosage rate of administration of estrogen and pyridoxal or its precursor is predetermined by a common dosage form or package for both.

Such composition may be combined with an estrogen composition in a common package. According to one embodiment the estrogen and the pyridoxal or said precursor are combined in a single dosage form. Alternatively the estrogen on the one hand and the pyridoxal or said precursor are wholly or in part provided each in separate dosage forms but in a common package.

In a particularly preferred embodiment the dosage form or dosage forms are arranged in the package in a pattern prescribing a dosage regimen over a treatment period equivalent to one or a plurality of menstrual cycles or selected portion(s) thereof. For example said pattern prescribes a dosage regimen adapted to the menstrual cycle. This will be analogous to conventional forms of packaging for oral contraceptives, wherein the package, adapted as a dispenser, has separate compartments, containing the tablets (or other oral dosage forms) for each day of the menstrual cycle or a predetermined portion or portions of such cycle. According to the invention, if the pyridoxal or precursor are contained in dosage forms separate from those containing the estrogen composition, these separate dosage forms may be contained in common compartments for each day or in separate compartments forming groups for each day.

Frequently oral contraceptive tablets are administered in such a way that treatment is divided into an active treatment period (e.g. 21 days) followed by a placebo treatment period (e.g. the following 7 days).

The present application provides for the incorporation of pyridoxal or its precursor into the active tablet as well as into the placebo tablets. Alternatively, pyridoxal administration may be restricted to the placebo tablets only or PL may be administered as a separate dosage form over all or part of the entire cycle, preferably the whole cycle, optionally lower dosage during active treatment.

In addition, the quantity of B6 vitamers in the active and placebo tablets are not necessarily identical. In one preferred variation for example, the quantity of pyridoxal in the active tablets (to be taken for 21 days) may be relatively low, e.g. 5 mg/tablet, whereas relatively more pyridoxal or precursor) is contained in the placebo tablet (e.g. 20 mg).

The new compositions and combinations aforesaid are part of the present invention.

The invention contemplates that the compositions and combinations may be supplied with appropriate instructions for carrying out the treatment or prophylaxis as herein described. Such instructions may be oral but are preferably in written, printed or pictorial form, e.g. included in or applied to a package containing the compositions.

As in other embodiments described above the compositions for counteracting side effects of estrogen many contain one or more of the said potentiators of pyridoxal. Once again The dosage forms of the compositions containing pyridoxal or said precursor may be adapted for oral use or for parenteral use. Oral dosage forms, in particular tablets and capsules but also syrups and drops are preferred. Particularly preferred are slow- or sustained-release forms.

In certain conditions a depot form may be appropriate.

Suppositories or pessaries can also be formulated. The active substance may in suitable circumstances also be provided as a dietary supplement or as part of a dietary food, in which form the pyridoxal or precursor is likewise partly absorbed and released to the patient relatively slowly and over a prolonged period.

Slow, sustained release of pyridcxal or the precursor is particularly inducive to maximum benefits from the relatively small dosages contemplated by this embodiment of the present invention.

Besides the advantage of greatly reduced dosage rates and the resultant absence of pyridoxine side effects, the use of pyridoxal or its precursors instead of pyridoxine offers a number of further advantages. The advantage of pyridoxal over pyridoxine as a source of vitamin B6 is especially conspicuous in its effects on estrogen induced derangements of lipid metabolism. It has recently been confirmed that while pyridoxine is only a weak lipid-lowering and regulating agent, pyri- B) genetic enzyme insufficiency, in particular oxidase deficiency or Polymorphic aberration C) Enzyme (e.g. oxidase and PLP-specific phosphatases) ihhibition due to
(i) disease-produced toxins, including polyamines
(ii) drugs;

As regards dosage forms and dosages, and Potentiators, essentially the same principles apply as in the earlier discussed cases.

| Vitamer | Route | Dosage rates for parenteral administration to children and adults | | | | | |
|---|---|---|---|---|---|---|---|
| | | Daily adult dose (mg) | | | Daily dose mg/kg bodyweight | | |
| | | Range | Preferred | Optim. | Range | Preferred | Optim. |
| PL | i.v. | 2–300 | 5–150 | 10–100 | 0,03–4.28 | 0.07–2.14 | 0.14–1.43 |
| PM | i.v. | 2–300 | 5–150 | 10–100 | 0.03–4.28 | 0.07–2.14 | 0.14–1.43 |
| PM | i.v. | 2–350 | 5–250 | 10–150 | 0.03–5.0 | 0.07–3.57 | 0.14–14 |
| PLP | i.v. | 2–350 | 5–250 | 10–150 | 0.03–5.0 | 0.07–3.57 | 0.14–2.14 |
| PL | i/m | 3–400 | 5–200 | 10–150 | 0.042–5.7 | 0.07–2.89 | 0.14–2.14 |
| PM | i/m | 3–400 | 5–200 | 10–150 | 0.042–5.7 | 0.07–2.89 | 0.14–2.14 |
| PLP | i/m | 5–450 | 10–300 | 20–200 | 0.07–6.42 | 0.07–4.29 | 0.28–2.86 |
| PMP | i/m | 5–450 | 10–300 | 20–200 | 0.07–6.42 | 0.07–4.29 | 0.28–2.86 |
| PL | s/c | 3–500 | 5–250 | 10–200 | 0.042–7.14 | 0.07–3.57 | 0.14–2.86 |
| PM | s/c | 3–500 | 5–250 | 10–200 | 0.042–7.14 | 0.07–3.57 | 0.14–2.86 |
| PLP | s/c | 7–500 | 10–300 | 10–250 | 0.10–7.14 | 0.14–4.280 | 0.14–3.57 |
| PMP | s/c | 7–500 | 10–300 | 10–250 | 0.10–7.14 | 0.14–4.28 | 0.14–3.57 |
| For oral administration | | | | | | | |
| PL | | | 2–500 | 5–250 | 10–200 | 0.03–7.2 | 0.07–3.6 | 0.14–2.9 |
| PM | | | 2–500 | 5–250 | 10–200 | 0.03–7.2 | 0.07–3.6 | 0.14–2.9 |
| PLP | | | 2–500 | 5–250 | 10–200 | 0.03–7.2 | 0.07–3.6 | 0.14–2.9 |
| PMP | | | 2–500 | 5–250 | 10–200 | 0.03–7.2 | 0.07–3.6 | 0.14–2.9 | doxal and its precursors have unexpectedly strong lipid lowering effects in experimental animals (U. Speck, German patent application P37 05 549.6. This difference in activity also persists in humans, and especially in cases of deranged lipid metabolism resulting from long term oral contraceptive usage.

One additional, crucially important, not previously known reason for the superiority of pyridoxal and the said precursors as a vitamin B6 supplement in the treatment or prophylaxis of depressed or inadequate intracellular pyridoxal phosphate levels arises from the unexpected discovery that a substantial percentage of patients suffer from an inherent intracellular partial or total inability to convert pyridoxine into pyridoxal phosphate. Such inability can be associated with some of the pathological conditions described further above. However, quite surprisingly about 20% of humans suffer from such relative inability genetically. This then takes us to the second major category of disturbed or insufficient PN-PLP pathways, i.e. inherent intracellular enzyme deficiency or defect.

The present invention provides a pharmaceutical or dietary composition and method of treatment for the supplementation of vitamin B6 deficiency in plasma and cells—tissue cells as well as blood cells—caused by pyridoxine—non-responsive conditions (or conditions that respond poorly to PN) due to newly discovered instances of enzyme (especially PN-oxidase) deficiency or polymorphism in organs and cells which are normally available for pyridoxine utilisation. Such deficiencies are of special clinical relevance under the following conditions:

A) cellular immaturity, for example in premature infants; excessive need for replacement of damaged or destroyed cells, which replacement may occur:
(i) from less specialised precursor cells
(ii) by normal cell division The dosage forms preferably include a suitable source of zinc, e.g. zinc chloride, zinc sulphate (or other physioloigically acceptable zinc salt) or zinc oxide, preferably in an amount suitable to provide a dosage of zinc of:

| | 10–20 mg per day as Zn (for adult) = 0.15–0.30 mg/kg/day |
|---|---|
| Range: | 0.05–0.9 mg/kg/day |
| Preferred: | 0.1–0.5 mg/kg/day |
| Optimal: | 0.15–0.3 mg/kg/day |

The dosage forms preferably include a suitable source of magnesium, e.g. pharmacologically acceptable salts of magnesium such as magnesium chloride or magnesium aspartate, or magnesium oxide; preferably in an amount suitable to provide a dosage of magnesium of:

| | 100–300 mg per day as Mg (adult) = 1.5–4.3 mg/kg/day |
|---|---|
| Range: | 0.5–10 mg/kg/day |
| Preferred: | 1.0–5.0 mg/kg/day |
| Optimal: | 1.5–4.3 mg/kg/day |

The different newly discovered situations involving inherent intracellular reduced capability or inability to utilise PN metabolically will be discussed more fully in what follows.

Cellular Immaturity

Premature infants: From a detailed comparison of the wide diversity of known facts with own findings it has now been concluded that full term infants are usually already able to convert dietary or pharmaceutically administered PN adequately to satisfy the substantial Vitamin B6 requirements of the growing body and its metabolism, but premature infants are not or not sufficiently so able, particularly not before a stage in gestational age which in most infants is between about 28 to 30 weeks. The lower the gestational age the more severe is this deficiency. The present inventor has been able to identify, as the primary cause of this deficiency, the inability of the immature system of the infant to produce the enzyme oxidase. The deficiency is aggravated by the defective tissue-oxygenation which is often present in premature infants.

To overcome this deficiency in premature infants using conventional pyridoxine supplementation would require several tens of times more than the expected dosage rate. However, such high dosages of pyridoxine are highly undesirable, particularly when administered in bolus form. Such high dosages will then exceed the capacity of the liver, and this in turn will result in excess pyridoxine in the plasma, from where it enters the various body cells (tissue and RBC) through the cellular membranes in competition with the limited supply of PL. Once inside the cell this PN now competes against intracellular PL for whatever kinase is available in the cell to form PNP instead of the required intracellular PLP. The PNP, which is useless in the absence of adequate oxidase activity, is trapped inside the cell there to compete further with PLP for vital enzyme sites. The above described phenomena resulting from excessive dosages of pyridoxine may result in toxic effects and (paradoxically) in symptoms similar to those of vitamin B6 deficiency.

Premature infants may be treated parenterally in the acute stages followed by oral administration of PL either in the form of paediatric drops or as an ingredient of an appropriately constituted infant food formula.

Suitable dosage rates are as follows:

| For parenteral administration to premature infants | | | | | |
|---|---|---|---|---|---|
| | | Range | | Preferred Range | |
| Vitamer | Route | Dose (mg) (daily) | Dose (mg/kg) bodyweight (daily) | Dose (mg) (daily) | Dose (mg/kg) bodyweight (daily) |
| PL | i.v. | 0.03–3.0 | 0.01–1.0 | 0.01–0.4 | 0.03–0.13 |
| PM | i.v. | 0.03–3.0 | 0.01–1.0 | 0.01–0.4 | 0.03–0.13 |
| PLP | i.v. | 0.06–6.0 | 0.026–1.0 | 0.02–0.5 | 0.06–0.16 |
| PMP | i.v. | 0.06–6.0 | 0.024–2.0 | 0.02–0.5 | 0.06–0.16 |
| PL | i/m | 0.05–6.0 | 0.017–2.0 | 0.02–0.5 | 0.06–0.16 |
| PM | i/m | 0.05–6.0 | 0.017–2.0 | 0.02–0.5 | 0.06–0.16 |
| PLP | i/m | 0.06–9.0 | 0.02–3.0 | 0.03–0.6 | 0.1–0.2 |
| PMP | i/m | 0.06–9.0 | 0.02–3.0 | 0.03–0.6 | 0.1–0.2 |
| PL | s/c | 0.05–6.0 | 0.017–2.0 | 0.02–0.5 | 0.06–0.16 |
| PM | s/c | 0.05–6.0 | 0.017–2.0 | 0.02–0.5 | 0.06–0.16 |
| PLP | s/c | 0.06–9.0 | 0.06–3.0 | 0.03–0.6 | 0.1–0.6 |
| PMP | s/c | 0.06–9.0 | 0.06–3.0 | 0.03–0.6 | 0.1–0.6 |

The active B6 vitamers may be supplied in lyophilised form in dark coloured ampoules sealed under nitrogen in convenient quantities. The contents may be dissolved in saline and added to the contents of any suitable infusion solution at a rate indicated above.

For Oral Administration to Premature Infants (i) Paediatric drops

These are formulated in an appropriately constituted flavoured base with added vitamins and minerals as in the accompanying example in such a manner that the following preferred dosage rates are achieved:

| | Range | | Preferred Range | |
|---|---|---|---|---|
| Vitamer | Dose (mg) (daily) | Dose (mg/kg) bodyweight (daily) | Dose (mg) (daily) | Dose (mg/kg) bodyweight (daily) |
| PL | 0.03–3.0 | 0.01–1.0 | 0.2–0.5 | 0.06–0.16 |
| PM | 0.03–3.0 | 0.01–1.0 | 0.2–0.5 | 0.06–0.16 |
| PLP | 0.05–5.0 | 0.016–1.6 | 0.3–0.6 | 0.1–0.2 |
| PMP | 0.05–5.0 | 0.016–1.6 | 0.3–0.6 | 0.1–0.2 |

The preferred vitamer is PL.

(ii) PL-fortified infant food

An infant food is formulated complying with all the usual requirements applicable to infant food formulae with regard to protein, energy, vitamin and mineral contents. B6 vitamers are included in such a manner that the daily intake is essentially as in the previous table.

The preferred vitamer is PL itself.

Alternatively tablets may be formulated for use with proprietary infant food formulae in such a manner that essentially the same amounts as listed above are administered. Such tablets are manufactured by processes known in the art in such a way that they will dissolve and disintegrate rapidly in aqueous media such as infant food formula dilute glucose solution or in fruit juices and the quantities per tablet may be such that the full dose is obtained in one tablet (to be used only once daily) or the daily dose may be subdivided over 2 to 6 tablets to be used with two feeds (e.g. morning and evening) or more often, e.g. with every feed.

In one preferred embodiment pyridoxal (or any one of the other vitamers listed) may be used in conjunction with a small quantity of pyridoxine (and riboflavine) in the form of both pediatric drops or tablets in order to stimulate liver enzyme development in the infants in such a manner that the following preferred dosage rates are achieved.

| | Range | | Preferred Range | |
|---|---|---|---|---|
| Vitamer | Dose (mg) (daily) | Dose (mg/kg) bodyweight (daily) | Dose (mg) (daily) | Dose (mg/kg) bodyweight (daily) |
| PL | 0.024–2.4 | 0.008–0.8 | 0.16–0.4 | 0.053–0.13 |
| PM | 0.024–2.4 | 0.008–0.8 | 0.16–0.4 | 0.053–0.13 |
| PLP | 0.04–4.0 | 0.013–1.3 | 0.24–0.5 | 0.08–0.17 |
| PMP | 0.04–4.0 | 0.013–1.3 | 0.24–0.5 | 0.08–0.17 |
| PN | 0.02–3 | 0.007–1.0 | 0.1–1.0 | 0.03–0.3 |
| Ribo- | 0.02–3 | 0.007–1.0 | 0.1–0.6 | 0.03–0.2 |

| | Range | | Preferred Range | |
|---|---|---|---|---|
| Vitamer | Dose (mg) (daily) | Dose (mg/kg) bodyweight (daily) | Dose (mg) (daily) | Dose (mg/kg) bodyweight (daily) |
| flavin | | | | |

Replacement of Damaged or Destroyed Cells

In the human or animal host the response to disease-induced or trauma-induced cellular damage is invariably growth stimulation to replace functionally incapacitated cells. Growth processes may include division of cells to produce daughter cells or it may involve cellular replacement through activation of a chain process by means of which non-differentiated precursor cells divide and ultimately develop through various stages to replace the damaged cells such as may occur after the destruction of red blood cells in disease.

In many cases, including normal healing, the regenerating cells go through a phase of rapid replication or, as in the case of red blood cell regeneration, precursor stem cells in the bone marrow proliferate to produce a series of intermediate cells culminating in an increased red cell population. The fundamental concept upon which this aspect of the present invention is based is that such rapidly regenerating cells have vitamin B6 growth requirements that differ from those of normal cells. This concept applies to individual cells, and to individual organs (e.g. the liver), and is thus analogous to the case of the premature growing infant or fetus.

In all cells, the basic requirements for growth are energy, proteins (amino acids), lipids, carbohydrates and a variety of co-factors (vitamins, minerals) which are necessary for optimal enzyme action. Amongst these, vitamin B6 activity is of special significance and is frequently a limiting factor due to the fact that B6 plays such a pivotal role in protein metabolism and energy production.

A particular application of this aspect of the invention relates to the replacement of highly differentiated cells from less differentiated precursor cells. Red blood cells (RBC) are important examples, as are other cellular elements of the blood. In all such cases the intermediate or more primitive precursor cells are better able and equipped to utilise PL rather than PN as a source of vitamin B6 activity.

A common undifferentiated primitive stem cell in the bone marrow gives rise to lymphocytes, red blood cells, granulocytes, monocytes, platelets and others in the course of which it is transformed into a variety of precursor cells. In the case of the RBC formation, this process involves the following:

Undifferentiated stem cell→Proerythroblast→Basophilic erythroblast
Polychromatic erythroblast→Acidophylic
erythroblast→Reticulocyte→Erythrocyte (RBC)

Similar cascades exist in the case of the other cellular elements in the blood including platelets. A fundamental observation was the fact that a bone-marrow aspirate containing the more primitive, undifferentiated cells was found to be incapable of converting PN into PLP or PL, thus demonstrating for the first time the absence of PNP-oxidase activity in such immature cells. This has extremely important practical significance, since the developing RBC require PLP for haeme and haemoglobin synthesis.

The normal mature RBC is perfectly capable of utilising PN as a source of B6 activity, wherefore in health, when no special demands exist for RBC formation, PN is an adequate source of B6 activity in RBC. However, in any disease process during which an increased demand for RBC production may exist, the rate of RBC production may be compromised if inadequate B6 activity inside the cells exists, and during such an emergency the required B6 activity cannot be supplied by supplementation with PN, since the stem cells from which RBC are formed are incapable or at best have a reduced capability of utilising PN for this purpose. The developing RBC require optimal B6 activity inside the cells for various reasons including the critical B6 requirement for haemoglobin synthesis and for energy production. In the RBC, 90% of energy is derived from the process of glycolysis, several steps of which are B6 dependent, including glucose production from glycogen (B6 dependent glycogen phosphorylase) and several transamination reactions. The process is also critically dependent on the free availability of adequate quantities of magnesium.

Having regard to the aforegoing, the invention according to a particularly important aspect thereof provides a pharmaceutical composition for the treatment of conditions involving a destruction or shortage of red blood cells and/or of haemoglobin, comprising a content of pyridoxal in a dosage form and concentration designed to deliver daily to a patient from 0,01 to 7,0 mg pyridoxal per kg body mass, the pyridoxal being optionally present in the form of a complex or soluble addition salt which in vivo readily releases pyridoxal.

The invention provides the means for a new treatment of such conditions involving a new therapeutic mechanism. It is applicable to a wide range of diseases involving a shortage of haemoglobulin-synthesising red blood cells and/or of haemoglobin.

A deficiency of haemoglobin in the blood is called anaemia, of which many types are known. They all cause pallor, fatigue and breathlessness. In severe cases the nervous system may be damaged permanently, and death may result. The direct conventional treatment of one form of anaemia usually involves the administration of iron to supplement an iron deficiency, iron being needed by normal mature erythrocytes for the synthesis of haemogoblin. However, this presupposes the availability of an adequate supply of erythrocytes capable of performing such synthesis. Many forms of disease result in a shortage of these cells.

Such diseases may involve failure of the bone marrow to produce sufficient red blood cells, causing aplastic anaemia. In the past this condition could only be relieved by transfusion, bone marrow transplantation or by marrow stimulating agents including vitamin B12.

Merrill and Henderson (Am. Rev. Nutr., 1987.7, 137056) on page 144 describe the treatment of "pyridoxine-responsive" anemias with pyridoxine. In spite of the relatively high dosages (50–200 mg PN/day) and in one case even 600 mg/day) the response rate was stated to be "optional" in fewer than half of the cases. The explanation given is not in accordance with applicant's findings. Other forms of anemia are non-responsive. The reference does not support the new approach according to the present invention. The toxic side effects of high dosages of PN are confirmed by what is stated on page 147.

Haemolytic anaemia is caused by excessive haemolysis of red blood cells, causing anaemia and jaundice. Such haemolysis may have several causes, one being the various protozoal diseases in man or animals, wherein the protozoa proliferate in and destroy the red blood cells. These include in man malaria (four different plasmodium species), bartonellosis, and in animals Rift Valley fever, corridor disease, biliary fever (Babesia canis).

Red blood cells are also destroyed by other types of micro organisms, e.g. certain viruses, such as parvo virus B19.

Some of the diseases which destroy red blood cells also destroy other cells, the regeneration of which is favourably influenced by the administration of pyridoxal or its precursors according to the invention, e.g hepatocytes in the case of malaria.

A further benefit resulting from the invention in the present context is the fact that toxins and polyamines are frequently released during disease which additionally compromise the ability of the body to utilise pyridoxine. Also, some of the drugs used in combatting such diseases have that side effect. Pyridoxal plays an important role in overcoming the resultant B6 deficiency.

In many diseases, blood polyamine levels rise sharply due to disease-induced cellular death and disintegration. Polyamines are essential constituents inside living cells, where they are essential for macromolecular synthesis, but increased concentrations outside cells such as may occur during certain diseases are toxic due inter alia to the fact that they are known to react chemically with PLP, the resulting complexes being eliminated in the urine. We have now surprisingly found that polyamines and/or other disease-produced toxins may also inhibit the B6-activating enzyme system as well as the natural PLP-hydrolysing phosphatases and that this is one of the mechanisms by which increased toxin and polyamine levels produced in disease are toxic. This is of particular relevance to RBC haemeostasis since, in general, disease-produced polyamines are to a large extent transported inside RBC, and specifically in the case of malaria there is a marked parasite-related increase of polyamines inside RBC, whereas normally there are only trace amounts of polyamines inside RBC. RBC infected with malaria parasites therefore have a reduced capacity to utilise non-phosphorylated B6 vitamers such as PN—a further advantage of supplementation with the appropriate B6 vitamer PL or PM. In addition, accumulated intraerythrocytic polyamines (in disease) will react and thus remove PL and PLP, thereby creating an increased demand for the production of these co-factors.

Anaemia may also be caused by abnormalities of the red blood cells, as happens in macrocytic anaemia or in sickle cell anaemia, and in many of these cases patients may benefit to a varying degree from the administration of PL.

Anaemia may result from nutritional causes or from severe blood loss, due to various causes, including menstrual abnormalities, and in such cases PL is superior to PN in restoring the B6 component of the deficiency.

It has now been discovered surprisingly that pyridoxal is capable of stimulating the formation of haemoglobulin even in many cases where conventional forms of therapy are ineffective or inadequate, and specifically in some cases of so-called "pyridoxine refractory" or "pyridoxine non-responsive" anaemias.

It follows from the aforegoing that the composition and method are specifically recommended for the treatment of the aforedescribed conditions, i.e. anaemia, malaria, babesia canis infections and others with similar metabolic features.

It follows further that the invention can be applied to improving blood transfusion preparations and blood substitutes by the incorporation therein of an appropriate content of pyridoxal or one of the substances referred to which release PL in vivo or similarly by one of the other non-pyridoxine type of B6 vitamers.

In contrast to some other vitamins, the physiology and biochemistry relating to B6 differs relatively little between humans and animals.

Accordingly, what has been described in the aforegoing in relation to humans is applicable also to veterinary medicine. Accordingly, the scope of the invention extends to veterinary medicine in relation to all aspects of the invention. The pharmaceutical compositions may be applied in the treatment of animal diseases and surgery substantially in a manner analogous to the treatment and prophylaxis described for humans.

A specific application would be in the context of game capture, and sedation and transportation of domestic or wild animals. For game capture the present invention teaches the inclusion of PL (optionally with other ingredients described above) in parenteral sedation and immobilising solutions, e.g. for darting syringes, as well as (and in particular) the inclusion of PL (and optional other ingredients) as part of or to be administered jointly with or in injectable antidote solutions as used in reversing the sedation and immobilisation after capture.

The following table summarises a number of microbial diseases in man or animals involving large-scale cell destruction by intracellular or extracelllular infections:

In that table a number of microbal diseases are shown. All of these are responsible for cell death of the "affected cells". The dead cells release polyamines and in many cases toxins are also released—either by the dead cells or the microbes or both, whereby PLP is depressed and the PN-PLP pathway is compromised. Where the affected cells are blood cells, they have to be replaced in the bone marrow by the "cascade" procedure described further above. These cells play an important role in the PN-PLP pathway. Stimulated by the increased cell demand these newly formed blood cells enter the circulation in an immature state in which they cannot yet perform their PN-PLP pathway function. The replacement of the remaining cells takes place by in situ cell division, followed by cell growth of these daughter cells. This process requires the availability of adequate amounts of PLP which the young cells themselves cannot supply and which availability is compromised by cell death. The invention shortcuts the PN-PLP pathway by the direct supply of PL which can enter the cells readily for in situ conversion into intracellular PLP.

| AFFECTED CELLS | INTRACELLULAR INFECTIONS | | | EXTRACELLULAR INFECTIONS |
| --- | --- | --- | --- | --- |
| | VIRUS | BACTERIA RICKETTSIA | PARASITE FUNGI | BACTERIA |
| Red blood cells | Parvovirus | | Malaria | |

-continued

| AFFECTED CELLS | INTRACELLULAR INFECTIONS | | | EXTRACELLULAR INFECTIONS |
| --- | --- | --- | --- | --- |
| | VIRUS | BACTERIA RICKETTSIA | PARASITE FUNGI | BACTERIA |
| T-lymphocytes | B19 HTLV-I; CMV HIV; HHV-6 | | | |
| B-Lymphocytes | EBV; HHV-6 | | | |
| Macrophage | | Mycobacteria Salmonella Listeria | Histoplasma Blastomyces | |
| Vascular endothelium | | Rickettsiae | | |
| Gut epithelium | Enterovirus | | Cryptosporidium Isospora | Shigella Salmonella Camphylobacter |
| Enterocyte | Rotavirus Adenovirus | | | |
| Non-keratinised squamous epithelium | Papillomavirus Herpes simplex virus | | | |
| Keratinised epithelium | Papillomavirus | | Dermatophytes | |
| Respiratory tract epithelium | Influenzavirus Resp sinsitielevirus | Mycoplasma | | |
| Glial cells/Neurones | Enterovirus Polyoma JC | | Toxoplasma | |
| Hepatocytes | Hepatitis A virus Hepatitis B virus Hepatitis D virus Hepatitis NANB viruses Yellow fever virus | | Toxoplasma Malaria | |

HTLV-I = Human T-cell lymphotropic/leukemia virus I
HIV = Human Immunodeficiency virus
EBV = Epstein Barr virus
CMV = Cytomegalovirus-6
HHV-6 = Human Herpesvirus-6

The above comments in the context of RBC, relating to toxins, polyamines and side effects of drugs used in the treatment apply also to many of these diseases.

In addition to the organisms in the above table, rickettsia are also to be considered in such diseases as epidemic typhus, Rocky Mountain spotted fever, Q-fever, heartwater (in cattle).

Genetic Enzyme Polymorphic Aberration

It has now been discovered quite unexpectedly that about 20% of a normal human population have a genetic aberration (polymorphism) in their enzyme system which impairs their ability to convert pyridoxine into pyridoxal. Of course, if that condition coincides with any of the situations giving rise to vitamin B6 deficiency even in otherwise "normal" persons, such persons are especially compromised when put on conventional pyridoxine supplementation. These are the so-called "poor responders" or "non-responders" to PN therapy.

The enzyme glutamate-pyruvate-transaminase (GPT) is a PLP dependent enzyme present in RBC which can be used to assess the utilisation of PN by RBC. In the population, individuals may be divided into 3 different groups corresponding to 3 polymorphic forms of the enzyme (1-1, 25%; 1-2, 50%; 2-2, 25%.

Approximately 20% of all persons studied (belonging to all 3 groups) were found to be slow responders to oral PN, RBC GPT-activity having been measured at day 0 and day 28 before and after daily oral supplementation with PN (10 mg).

It has now been found that these slow reactors have a genetically determined PN-oxidase enzyme defect.

The presence of 20% "slow-reactors" in the population now explains for the first time why in a variety of so-called B6 responsive diseases (premenstrual tension, depression, anaemia) it has frequently been found that approximately 80% of patients respond well to the drug but that the response rate is seldom 100%.

We have now surprisingly found that such patients have reduced PN-oxidase activity and that they do respond much more satisfactorily to PL or PM administration than to PN.

The above novel observations have important clinical implications. Twenty percent of all patients previously discussed (e.g. in infections affecting RBC B6 status or infection similarly affecting B6 status of other cells or otherwise compromised B6 status due to serious disease or drugs) will be more seriously at risk than the remaining 80%. A further aspect of the present invention provides for a suitable test to determine intracellular PN-oxidase activity and thus to identify such patients which may then receive early and preemptive treatment as discussed more fully below.

In applying the present invention it is furthermore proposed to combine this with appropriate quantitative or semi-quantitative diagnostic tests for PNP-oxidase activity in tissue homogenates and red blood cell haemolysates. Such tests may be used to identify patients suffering from the aforesaid genetically impaired oxidase activity, who are particularly at risk in any situation where vitamin B6 supplementation is needed and who then definitely require the administration of a source of B6 other than pyridoxine.

Such test may also be employed to identify and quantify the extent of any oxidase deficiency to which this invention relates.

A suitable simplified assay will be described by way of example which may be modified to suit particular requirements. In addition, a more accurate method based on HPLC measurement of the B6 vitamers involved in the reaction will be also described.

By the judicious application of the teachings of the present invention to suitable clinical situations it has been found possible to enhance the success of conventional forms of treatment.

EXAMPLE 1

Quantitative Assay of PNP-oxidase Activity in Tissue and Homogenates and Red Blood Cell Haemolysates N-(5'-phospho-4'-pyridoxyl)-N'(naphthyl)ethylenediamine (800 micromoles) was added to 3.5 ml of 0.2 M Tris buffer (pH 8.0) in screw-top test tubes, and the mixture equilibrated by shaking in a water bath at 37° C. An enzyme source (tissue homogenate red blood cell haemolysate, 0.1–0.5 ml) was added, and the uncapped tubes allowed to incubate with shaking for 60 min, after which 1.0 ml of 10% NaOH was added to each tube. Tubes were removed from the water bath and 5.0 ml of special grade ethyl acetate added. The tubes were closed and then shaken vigorously for 3 min. The fluorescence in the organic phase was then read (excitation 320 nm, emission 410 nm).

Enzymic activity was expressed as nanomoles of products formed/h/0.1 ml of enzyme source.

EXAMPLE 2

Procedure for Detecting Oxidase Deficiency in Red Blood Cell (RBC) Haemolysates

The principle of the procedure is as follows: A RBC haemolysate is prepared to serve as the oxidase enzyme source. The haemolysate is then allowed to react with a standardised quantity of pyridoxamine phosphate (PMP) under controlled conditions (time of reaction, pH, temperature), and during this period PMP is oxidised by the enzyme to both pyridoxal phosphate (PLP) and pyridoxal (PL). The quantity of PLP+PL formed under these conditions is a direct indication of the amount of oxidase enzyme present, and thus the amount of oxidase present in the RBC haemclysate reflects the patient's oxidase enzyme status, which is expressed in terms of nanomol PLP formed per hour per gram of haemoglobin (nmol PLP/h/g Hb).

The amount of PLP+PL may be determined either by means of fluorescence analysis (of the complexes formed by PLP+PL with semi-carbazide) or by means of HPLC methodology (which also allows for individual measurement of PLP and PL).

The fluorescence procedure may be adapted for use in automated equipment, thus allowing for the routine analysis of large numbers of samples, as detailed in the following example.

Assay of Pyridoxamine Phosphate Oxidase (PPO)

Packed RBC haemolysate (0.125 ml) was diluted to 500 μl with potassium phosphate buffer (0.133 M, pH 8.0) and 50 μl was withdrawn for haemoglobin measurement by the cyanmethaemoglobin method (Blood 1957 12, 1132).

To the remaining 450 μl, pyridoxamine-5-phosphate was added to give a final concentration of 8 μM. After 2 h incubation, the reaction was stopped with an equal volume of trichloracetic acid (10% w/v) and the precipitated protein removed by centrifugation.

The protein-free extract was then used for the determination of PLP +PL either by means of automated fluorometric analysis or by mean of an HPLC procedure.

In the fluorometric assay, an aliquot of each protein-free extract after incubation was transferred to a sample cup of a centrifugal analyser which was programmed to mix 1 vol. sample with 3 vols. of a buffer, pH 9.5 containing KHOO₃ (32.5 g/l) and K₂CO₃(24.1 g/l), and this was followed by 0.2 vols. of 12% (w/v) of semicarbazide hydrochloride.

The development of the fluorescent adduct with PLP and PL was then measured after 15 min. at 37° C. (peak excitation wave length 360 nm) with a broad emission filter peaking at 450 nm. The amount of PLP+PL formed was determined by using standards over the range 0.05–0.8 uM.

Identification of Subjects Genetically Deficient in the Enzyme Pyridoxamine Phosphate Oxide (PPO)

Using the above analytical system, the following cut-off point is adopted with allows for the identification of genetically deficient individuals.

| Type of patient | n mol PLP + PL/g Hb/h |
|---|---|
| Normal | above 4.30 |
| Genetically deficient | below 4.30 |
| Example 3 | |
| Alternative PMP (PN) - oxidase activity measurement | |
| Principle: | |
| oxidase | |
| PMP    PL + H₂O₂ + NH₃ | |
| | α-ketoglutarate |
| as substrate    NADH | |
| (standard        ADP glutamate dehydrogenates | |
| solution) | |
| (or PNP) | |
| NAD    cofactor | |
| L-Glutamate | |

The released NH₃ is detected by the NADH-dependent glutamatedehydrogenase reaction. NH₃ is converted by α-keto glutarate with NADH (reduced form of nicotine adenine dinucleotide) as coenzyme into L-glutamate. ADP (adenosine diphosphate) is a further cofactor and GLD (glutamate dehydrogenase) is the actual enzyme for that reaction. NADH is used up and this consumption is measured. The decrease in the absorption (ΔE) of NADH corresponds to the activity of the oxidase enzyme. The combined reactions have a strong pH optimum at pH 7.5–7.6. Added ADP is a required co-factor for the GLD reaction.

Method:
Buffer I: 0.1 M TRIS—HCl, pH 7.5 (12.1 g/l)
Buffer II: 0.5 M TRIS—HCl, pH 7.5
Preparation of haemolysates:
0.5 ml Buffer I
0.1 ml packed washed red cells
0.05 ml 10% aqueous solution of TRIION-X-100
Reagent mixture:
In 10 ml Buffer I dissolve 20 mg PMP.

Add 0.5 ml reagent mixture in reaction tube and start reaction with 0.1 ml of haemolysate in 30° C. waterbath in the dark. Incubate for 0 and 90 min for each haemclysate sample. Stop reaction and denature hemoglobin by adding 500 µl of 1N HCl and after 5 min adding 500 µl of 1N NaOH. Add 700 µl of $CHCl_3$, shake vigorously to precipitate denatured hemoglobin and centrifuge for 10 min at 10,000 G to remove haemoglobin from the supernatant of the haemoglysate which is retained.

Photometric $NH_3$—detection:
Dissolve

| | |
|---|---|
| 20 mgα-ketoglutarate (Na-salt) | (Boehringer) |
| 10 mg ADP | (Boehringer) |
| 6 mg NADH | (Boehringer) |
| in 10 ml Buffer II | |

Pipette into cuvette:
1.4 ml of supernatant of haemolysate (see above) and add
0.6 ml of above solution in Buffer II
Measure OD at 365 nm (to determine initial NADH concentration).
Add 20 µl of glutamate-dehydrogenase in glycol (Boehringer) to start $NH_3$ consuming reaction
Measure OD again when OD has stabilised (end-point).
Perform Hb determination on haemolysate.

ΔE values (change in OD at 365 nm) obtained in this manner reflect oxidase enzyme activity. Final enzyme activity values are recorded as ΔE/g haemoglobin/h.

All reagents used must be essentially $NH_3$ free. Addition of riboflavin and/or FMN has no influence.

The following typical results were obtained in a healthy adult human population:
Erythrocyte oxidase activity:
Normal patients 20–150 µE/g Hb/h. Patients with deficient oxidase activity: below 20 ΔE/g Hb/h.

EXAMPLE 4

Clinical Trials on Dogs With B. Canis Infection

*Babesia canis* infection, better known as "biliary fever", is a severe and frequently fatal disease in dogs. It is a protozoal disease involving large-scale destruction of erythrocytes (red blood cells) and loss of haemoglobin. Double blind trials were carried out on two groups of dogs presented to the clinic for treatment of severe *B. canis* infections. Upon admission, all animals were recumbent with fever, jaundice, and accelerated heart and respiratory rate. All animals were given standard treatment, which consisted of post surgical drip, doxycycline, trypan blue, hepavet, electrolytes and glucose. In the experimental group, a solution of PL was added to the drip (electrolytes, glucose) given to the animals. In the control group, saline was given to replace the PL solution.

The PL solution according to the invention was made up as follows (per vial):

| | |
|---|---|
| Pyridoxal hydrochloride | 243 mg (= 200 mg PL) |
| Ascorbic acid | 10 mg |

Experimental Treatment

Experimental animals: PL solution according to the invention was given with the drip in such a manner that each patient received 50mg of pyridoxal over a 12 h period. Each animal received only one such course of treatment.

Control Animals

These received saline instead of PL solution under similar conditions. Control animals were selected to resemble experimental animals as closely as possible in respect of race and initial haemoglobin concentration. The results are given in the following table.

| | Hb* (g/l) | RCC ($\times 10^{12}$/l) | Ht (l/l) | MCV (fl) | MCHC (g/dlRC) | WCC ($\times 10^9$/l) |
|---|---|---|---|---|---|---|
| E** | 11.0 | 0.41 | 2.1 | −6 | 3.8 | 3.0 |
| E | 12.8 | 0.49 | 4.2 | 2 | −1 | −8.4 |
| E | 6.5 | 0.47 | 3.6 | 0 | −2.5 | 2.5 |
| E | 9.5 | 0.41 | 4.2 | 3 | −1.7 | 3.1 |
| E | 7.8 | 0.23 | 2.3 | 1 | −0.5 | 1.05 |
| E | 24.8 | 0.64 | 5.4 | 1 | 2.5 | 17.9 |
| Total | 70 | 2.65 | 21.8 | 1 | −8.2 | 27.15 |
| Average*** | 11.7 | 0.44 | 3.63 | 0.17 | −0.03 | 4.52 |
| C | 3 | 0.18 | 1.19 | 1.25 | −1.5 | −3.4 |
| C | 12 | 0.53 | 4.1 | −1.7 | 0 | −4.4 |
| C | 2 | −0.01 | 1.0 | 12 | 7 | 17.8 |
| C | −1 | −0.04 | 0.8 | 6.0 | −2.7 | −0.5 |
| C | 9 | 0.42 | 3.7 | −1.2 | −1.4 | 2.1 |
| C | 6.8 | 0.24 | 3.9 | 0.3 | 4.3 | −7 |
| Total | 31.8 | 1.31 | 12.9 | 18.3 | −2.9 | 4.6 |
| Average | 5.3 | 0.22 | 2.55 | 3.17 | −0.48 | 0.76 |

Hb*: Haemoglobin (g/l)
RCC: Red cell count ($\times 10^{12}$/l)
Ht: Haematocrit (l/l)
MCV: Mean corpuscular volume (fl)
MCHC: Mean corpuscular haemoglobin content (g/dlRC)
WCC: White cell count ($\times 10^9$/l)
**E: denotes experimental animals C: denotes controls, E: denotes changes per day during the period between the first two series of measurements of the parameters listed. Normally these represent measurements obtained immediately after admission (or 1 day later) and again 2 to 4 days later after treatment has been started.
***Average changes for six animals in each group over the two periods of measurement.

CONCLUSIONS

Clinical: The clinical observation was that animals on the PL infusion responded much better to treatment than controls. These animals were significantly improved after 2 to 3 days judged on the basis of movement, water and feed consumption and alertness. Normally, as in the case of the controls, the animals only reach this stage of clinical improvement, if at all, after 5 to 6 days.

Haematological: Large, significant differences are reflected in several important parameters between experimental and control groups (haemoglobin, RCC, WCC). These are fully consistent with the clinical observations. Inter alia, there had been an amazing recovery of haemoglobin levels, substantially in excess of what could be explained in terms of normal rates of formation of new mature red blood cells, capable of synthesising haemoglobin in the normal manner.

This example illustrates the benefits of PL administration in diseases involving destruction of erythrocytes. It has far-reaching implications and applications far beyond biliary fever in dogs. The erythrocytes are formed in the bone marrow, where (in humans) they take about 120 days to mature into cells capable of synthesising haemoglobin. For this synthesis pyridoxal phosphate is needed; however, the availability of pyridoxal phosphate depends on the availability of adequate activity of certain enzymes, in particular oxidase. In the immature erythrocytes a shortage of oxidase prevails, resulting in a shortage of pyridoxal phosphate and a resultant compromised ability to synthesise haemoglobin. In many pathological conditions the enzymes responsible for the formation of pyridoxal phosphate are, moreover, inhibited. In addition, the biogenic polyamines released in some pathological conditions leading to anaemia (as in biliary fever), as well as medications conventionally employed in the treatment of these diseases, aggravate the shortage of pyridoxal needed for haemoglobin synthesis.

Further Clinical Trials on Dogs With *B-canis* Infection

The experiment was repeated with 13 dogs (10 inbred beagles and 3 other mongrels) randomly divided into an experimental and a control group. All animals were infected with *Babesia canis* by injection of blood from a splenectomised donor dog which led to the development of acute Babesiosis in approximately 3-5 days. All dogs were monitored twice daily until the haematocrit values fell to 0.15 l/l when treatment was started which in the case of all animals consisted of the following:

Electrolytes solution (number 2) for the first 24th, thereafter Post-Surgisol. Both fluids were administered by means of an intravenous jugular catheter at a rate of 80 ml/kg/24h.

Trypan blue (1%) 1 ml/kg intravenous once only. Berenil 3.5 mg/kg intramuscularly 7 days after the Trypan blue. Heparin, 25 IU/kg subcutaneously three times per day for the first 2 days.

Experimental animals, in addition, received pyridoxal in their infusions at a concentration of 50 mg/l for the entire duration of fluid therapy.

Before the start of treatment, a urine dipstick and sediment examination were performed as well as a complete clinical evaluation and faecal flotation to determine the presence of helminth ova.

Assessment: Temperature pulse and respiration were measured every 6 hours during the first 3 days and a subjective assessment of habitus (grade 1-4) and appetite (1-4) was also made at the same time.

Full haematological and biochemical assessment was performed daily.

Serum alkaline phosphatase determinations were made on days 1 and 3.

Additional trial parameters and measurements consisted of Astrup determinations (before treatment and again 24 hours later) and a ten day survival rate.

Samples for haematology were drawn in evacuated EDTA tubes and for serum chemistries into plain evacuated tubes (cephalic vein).

Plasma PLP and PL as well as RBC-PLP and PL values were determined by means of a HPLC procedure routinely used for human studies.

The following results were obtained.

Two animals died in the control group and none in the experimental group. There was a definite clinical improvement in the experimental group consistent with the observations in the first experiment.

During the first 3 days (the decisive period which determines survival or not) there were significant differences in normablast count profiles: a continuous downward trend in the control animals and an inverse trend in the experimental group. Reticulocyte counts responded quicker in the experimental.

Whereas alkaline phosphatase values decreased in the control group from day 1 to day 3, there was a large increase in this parameter in the experimental group. Differences between the 2 groups were large and a definite trend discernable.

The mean corpuscular volume and the mean corpuscular hemoglobin were statistically significantly increased in the experimental animals at day 5.

EXAMPLE 5

Pyridoxal Infusion

Dissolve in sterile distilled water and dilute to 100 ml:

| | |
|---|---|
| pyridoxal hydrochloride | 4860 mg (= 4000 mg pyridoxal) |
| ascorbic acid | 1000 mg |
| sodium dihydrogen phosphate | 40 g |

Adjust pH to 6.5

Distribute 5 ml portions in amber coloured ampoules and lyophilise. Heat sterilise (10 min).

Administer as an infusion by dissolving in sterile saline and admixing the appropriate quantity with any other standard infusion or drip that the patient may be receiving (electrolytes, glucose) so that the dosage rates for parenteral administration as detailed herein will be achieved.

Alternatively, dissolve in 5-10 ml sterile saline and administer by intramuscular injection to achieve the dosage rate as specified herein.

EXAMPLE 6

Examples of Stabilised Solutions of PL a) To 100 mg of PL in 20 ml pH 7.0 Sørensen buffer (0.05 M) are added:

| | |
|---|---|
| Sodium metabisulphite: | 30-72 mg |
| Glucose: | 68-136 mg |
| Vitamic C: | 20 mg |

Filter seal in brown ampoules.
Heat sterilise at 50° C., 10 days.

Make up to 100 ml with sterile, distilled water and finally sterilise by filtration. Store in brown ampoules under nitrogen. To be used as in previous example.

EXAMPLE 7

Pyridoxal-supplemented Blood Substitute or Plasma

Pyridoxal hydrochloride (e.g. in sterile, amber coloured ampoules containing 200 mg of pyridoxal) is dissolved in 5 ml sterile saline solution and transferred to any commercially available blood substitute or transfusion solution in such a manner that, during infusion, the quantity of pyridoxal administered to the patients will be essentially as hereinbefore specified.

EXAMPLE 8

Pyridoxal-fortified additive for Use With Conventional Plasma Expanders and Blood Transfusion Dissolve in 100 ml of sterile water and adjust pH to 6.5:

| | |
|---|---|
| Pyridoxal.HCl | 4860 mg |
| Ascorbic acid | 1000 mg |
| Sodium dihydrogen phosphate | 40 g |

Distribute in 5 ml amber coloured ampoules and lyophilise.

Dissolve contents of ampoule in 5 ml sterile saline and add to infusion solution (blood, plasma, plasma expander) on the following basis:

1 ampoule per 2-5 l.

EXAMPLE 9

Use of Pyridoxal in the Treatment of Malaria

Two groups of malaria patients are treated with pyridoxal. All patients receive standard treatment considered appropriate by the clinician in attendance consisting of anti-parasitic medication with supporting therapy to combat anaemia and possible lactate acidosis.

Clinical Protocol

Group 1:

These are seriously ill patients with malaria according to the WHO criteria for severe complicated malaria. Haemoglobin values are below 10 g/dl in these patients with cerebral malaria who are treated in an ICU. Generally the patients present with renal failure (creatinine 250 u mol), respiratory failure, severe electrolyte and acid-base imbalance, severe parasitaemia (more than 5% infected cells), bilirubin more than 50 u mol/l; hypotension with bleeding abnormalities.

The patients receive normal standard treatment. In addition, the patients are given pyridoxal (200 mg per ampoule) by dissolving the contents of one ampoule in 5 ml sterile saline and adding the resulting solution to a standard electrolyte infusion solution. The rate of administration is such that the patients receive 100 mg pyridoxal/24h for the first 3 days and thereafter 50 mg/day for another 2 days.

Group 2:

These are less severely ill patients or patients recovering from severe malaria. They are treated conventionally in addition with pyridoxal (or less preferably pyridoxamine) by oral administration at a dosage rate as described above, in a slow-release form. Suitable dosage forms are described in Examples 10 and 11.

EXAMPLE 10

Oral Slow-release Tablet

A granulate is prepared having the following composition (per tablet): Pyridoxal.HCl 12.12 mg, emcompress (insoluble dicalcium phosphate filler) 125 mg, 5% gelatine sol. q.s. The granules are mixed with (per tablet) 125 mg emcompress, Natrosol (hydroxy ethyl cellulose) 125 mg, magnesium stearate 6.3 mg, and further 5% gelatine gel 9.5, mixed in a turbulo mixer and pressed into tablets.

EXAMPLE 11

Example 10 is repeated, using pyridoxamine.HCl instead of pyridoxal.HCl.

EXAMPLE 13

Pyridoxal-fortified Additive for Use in Infant Foods

A pyridoxal-fortified additive is formulated as follows:

| | |
|---|---|
| Pyridoxal.HCl | 10.0 mg |
| Homogenised powdered milk | 100 g |

The additive may be added to any infant feed formula (preferably of the humanised type) on the basis of 1.0 g of additive per kg bodyweight per day.

EXAMPLE 14

Pyridoxal-fortified Infant Food Formula

A basic infant food formula is composed in the usual manner containing powdered homogenised milk powder with added lactose, coconut and corn oil, and sodium citrate such that the composition is as follows:

Protein 1.6%; fat 3.3%; carbohydrate 67.0%.

The following quantities of vitamin and minerals are added per 20 g of this product:

| | |
|---|---|
| Pyridoxal.HCl | 0.08 mg |
| Vitamin A | 50 IU |
| Vitamin C | 4.0 mg |
| Vitamin D2 | 50 IU |
| Vitamin E | 0.5 mg ($\alpha$-tocopherol) |
| Vitamin B | 0.06 mg |
| Vitamin B2 | 0.07 mg |
| Vitamin B12 | 0.17 mg |
| Niacin | 1.0 mg |
| Ca pantothenate | 0.3 mg |
| Folic acid | 5.0 mg |
| Pyridoxine.HCl | 0.02 mg |
| Citric acid | 0.013 |
| Iron (as Fe fumarate) | 2.0 mg |
| Calcium (as calcium gluconate) | 10 mg |
| Magnesium (as Mg ascorbate) | 5 mg |
| Zinc (as Zn gluconate) | 0.2 mg |
| Iodide (as KI) | 7.0 mg |

Before use, 3.0 g are dissolved in 25 ml of water. 60-150 ml per kg bodyweight are given to premature infants during the first few days of life, with subsequent appropriate increases and adaptations.

EXAMPLE 15

Pyridoxal-containing Paediatric Syrup

| Composition per ml: | |
| --- | --- |
| Vitamin A | 50 IU |
| Vitamin B | 0.06 mg |
| Vitamin B2 | 0.07 mg |
| Pyridoxal hydrochloride | 0.08 mg |
| Pyridoxine hydrochloride | 0.02 mg |
| Glycine | 0.1 g |
| Vitamin B12 | 0.17 mg |
| Propylene glycol | 0.1 g |
| Nicotinamide | 1.0 mg |
| Vitamin C | 4.0 mg |
| Vitamin D2 | 50 IU |
| Pantothenic acid | 0.3 mg |
| Citric acid | 0.013 mg |
| Iron (as Fe fumarate) | 2.0 mg ($Fe^{++}$) |
| Calcium (as Ca gluconate) | 60 mg |
| Magnesium (as Mg ascorbate) | 8 mg |
| Zinc (as Zinc gluconate) | 0.5 mg |
| Potassium iodide | 7.3 mg |
| Lysine hydrochloride | 1.5 mg |
| Choline chloride | 0.5 mg |
| α-Tocopherol | 0.5 mg |
| Folic acid | 5.0 mg |
| Sodium saccharin | 2 mg |
| Sodium cyclamate | 10 mg |
| Keltrol F | 2 mg |
| Excipients | 25 mg |

1.0 ml/kg bodyweight is administered daily.

EXAMPLE 16

To confirm the inability of immature cells to convert pyridoxine into pyridoxal and its phosphate, an aspirate of bone marrow was tested. It was incapable of converting pyridoxine into pyridoxal, demonstrating the absence of adequate oxidase activity in premature red blood cells.

EXAMPLE 17

Pediatric Tablets 3 types of tablets are prepared having the following compositions:

| | Per tablet (A) | Per tablet (B) | Per tablet (c) |
| --- | --- | --- | --- |
| PL | 0.21 mg | 0.10 | 0.04 |
| PN | 0.06 mg | 0.03 | 0.012 |
| Riboflavin | 0.24 mg | 0.12 | 0.05 |
| Anhydrous lactose | q.s. (30–40 mg) | | |

Daily dose:
Tablets A: 1 tablet
Tablets B: 2 tablets
Tablets C: 5 tablets

The soluble tablets are added in accordance with the daily supplement regimen to a conventional feed formula.

EXAMPLES 18 to 20

These are suitably formulated as sterilised solutions having the compositions indicated (per 1000 ml of solution). In all cases due provision is made for osmolality requirements by addition of NaCl or by dilution.

The compositions given below may also be provided in powdered form (in the proportions indicated) in sterile ampoules or other containers, for dissolution in sterile water and dilution to a prescribed volume immediately before use.

EXAMPLE 18

General Solution for Intravenous Administration

| | Range | Preferred range | Preferred |
| --- | --- | --- | --- |
| (a) | | | |
| Pyridoxal.HCl* | 2–1000 mg | 20–100 mg | 50 mg |
| Glucose | 1–100 g | 20–80 mg | 50 g |
| $ZnCl_2$ | 1–1000 mg | 5–15 mg | 10 mg |
| Ascorbic acid | 1–5000 mg | 50–500 mg | 100 mg |
| (b) | | | |
| Pyridoxal.HCl* | 2–500 mg | 20–300 mg | 100 mg |
| $ZnCl_2$ | 1–1000 mg | 5–15 mg | 10 mg |
| Ascorbic acid | 1–5000 mg | 50–500 mg | 100 mg |

*May be varied as desired to provide for an infusion rate per hour of PL of 5 to 500 mg (preferred 50 mg) in humans.
Infusion rates (in both cases) using the compositions according to the last column: 50 to 150 ml/h

EXAMPLE 19

Solution for the Treatment of Shock a) Ringer's lactate solution

| NaCl = | 6.0 g; | Sodium lactate = | 3.2 g; |
| --- | --- | --- | --- |
| KCl = | 400 mg; | $CaCl_2.H_2O$ = | 270 mg; |

Pyridoxal.HCl* = 1 to 1000 mg (preferred range: 20 to 200 mg; preferred: 100 mg.
* May be varied as desired to provide for an infusion rate per hour of PL of 5–500 mg (preferred 50 mg).) in humans;
Zinc chloride = 1 to 1000 mg (preferred range; 5 to 15 mg; preferred: 10 mg);
Ascorbic acid = 1 to 5000 mg (preferred range: 50 to 500 mg; preferred: 100 mg).
This solution contains electrolytes in mmol/l as follows:
Na = 131, K = 5, Ca = 2, Cl = 111, lactate as $HCO_3$ = 29, and has millosmol/l of about 279 and pH of about 6.5.

b) Electrolyte solution;

| NaCl = | 6.0 g; | $NaHCO_3$ = | 2.3 g; |
| --- | --- | --- | --- |
| KCl = | 300 mg; | $MgCl_2.6H_2O$ = | 300 mg; |

Pyridoxal.HCl* = 1 to 1000 mg (preferred range: 20 to 200 mg; preferred: 100 mg.
*May be varied as desired to provide for an infusion rate per hour of PL of 5–500 mg (preferred 50 mg).) in humans;
$ZnCl_2$ = 1 to 1000 mg (preferred range: 5 to 15 mg; preferred: 10 MG);
Asorbic acid 1 to 5000 mg (preferred range: 50 to 500 mg; preferred: 100 mg).
Rate of infusion: 1.0 to 1.5 ml/kg/h.
This solution contains electrolytes in mmol/l as follows: Na = 130, K = 4, Mg = 1.5, Cl = 109, $HCO_3$ = 28 and has milliosxol/l of 273 and pH of 7.4.

EXAMPLE 20

Solution for Intravenous Infusion

| | Range | Preferred Range | Preferred |
| --- | --- | --- | --- |
| Pyridoxal.HCl* | 2–1000 mg | 20–100 mg | 50 mg |
| Pyridoxine.HCl | 1–1000 mg | 2–20 mg | 5 mg |
| Glucose | 1–100 g | 20–80 g | 50 g |
| Glutamate | 1–500 mg | 4–200 mg | 100 mg |
| $ZnCl_2$ | 1–500 mg | 5–15 mg | 10 mg |
| $MgCl_2$ | 5–5000 mg | 100–500 mg | 399 mg |
| Riboflavine | 1–100 mg | 5–20 mg | 10 mg |

-continued

| | Range | Preferred Range | Preferred |
|---|---|---|---|
| Ascorbic acid | 1–5000 mg | 50–500 mg | 100 mg |
| NaCl | | (as required) | |

*May be varied as desired to provide for an infusion rate per hour of PL of 5 to 500 mg (preferred 50 mg) in humans.

Preferred rate of infusion: 1.0 to 1.5 ml/kg/h.

EXAMPLE 21

Per os (One daily dose)

| | |
|---|---|
| PL | 10–500 mg, e.g. 200 mg |
| PN | 10–500 mg, e.g. 200 mg |
| Riboflavine | 1–100 mg, e.g. 10 mg |
| $ZnCl_2$ | 1–100 mg, e.g. 50 mg |
| $MgCl_2$ | 1–5000 mg, e.g. 2000 mg |
| Ascorbic acid | 100 mg |

Given as a solution or in the form of tablets or capsules, preferably in a slow release formulation.

EXAMPLE 22

Suppositories

| | |
|---|---|
| PL | 10–500 mg, e.g. 200 mg |
| PN | 10–500 mg, e.g. 200 mg |
| Riboflavine | 1–100 mg, e.g. 10 mg |
| $ZnCl_2$ | 1–50 mg, e.g. 20 mg |
| $MgCl_2$ | 1–2000 mg, e.g. 1000 mg |
| Ascorbic acid | 100 mg |

These ingredients to be included with the usual excipients, carriers, etc. used in the formulation of suppositories.

EXAMPLE 23

Immobilising/Sedation Composition for Game Catching or Transport a) As an additive to the drug, or to be administered separately: (per 100 kg live mass)
PL: 10–2000 mg, e.g. 200 mg
PN: 10–100 mg, e.g. 50 mg b) As an additive to the antidote solution, or to be administered separately: (per 100 kg live mass)
PL: 10–2000 mg, e.g. 200 mg
PN: 10–500 mg, e.g. 100 mg
Riboflavine: 1–100 mg, e.g. 10.5 mg

EXAMPLE 24

Treatment of a Patient During Immediate Post Infarction Period

Procedure A

In addition to the other drugs that may be indicated and that are conventionally administered, the following solutions are administered by means of intravenous infusion:
Initial period (0 to 2 hours post-infarction):
Composition per liter: NaCl: 6.0 g, $NaHCO_3$: 2.3 g, KCl: 300 mg, $MgCl_2.6H_2O$: 300 mg, Pyridoxal.HCl: 400 mg, rate of infusion: 80 to 120 mg/h (1 to 1.5 mg/kg/h).
Maintenance period: (2 to 12 h post-infarction):
Composition per liter: NaCl: 6.0 g, $NaHCO_3$: 2.3 g, KCl: 300 mg, $MgCl_2.6H_2O$: 300 mg, Pyridoxal.HCl: 100 mg. Rate of infusion: 80–120 ml/h (1–1.5 ml/kg/h Procedure B Initial period (0 to 2 h post-infarction):
Composition per liter: Glucose: 50 g, Pyridoxal: 100 mg,
Pyridoxine: 100 mg, Riboflavine: 5 mg, $ZnCl_2$: 10 mg.
Rate of infusion: 1 to 2 ml/kg/h.

EXAMPLE 25

Administration of Pyridoxal Containing Infusions to Critically Ill Patients

Composition per liter: NaCl: 6.0 g, $NaHCO_3$: 2.3 g, KCl: 300 mg, $Mg Cl_2.6H_2O$: 300 mg, Pyridoxal.HCl: 400 mg.
Low rate of infusion: 50 ml/h
Intermediary rate of infusion: 80 ml/h
High rate of infusion: 120 ml/h

EXAMPLE 20

Protective Effect of PL in Experimetally Induced Septic Shock in Animals (Rats)

An *E. Coli* suspension was prepared and serially diluted to the point where an injection of 0.3 ml caused approximately 80% mortality in rats after 12 h. This solution was used as the challenging solution in the following experiment:

Two groups of 6 male rats each were used. The animals were carefully selected so that the average mass in both groups was 210 g (191–219 g in the control group; 194–224 g in the experimental group). A solution containing 43.8 mg/ml of pyridoxal was prepared for i/v and i/p injection. 0.8 ml of this solution afforded 1.0 m mol/kg of PL when injected into a 210 g rat.

At time 0 h, the control group received 0.3 ml saline and the experimental group 0.3 ml of the PL solution. After 1 h all animals in both groups were challenged with 0.3 ml i/v of the *E. Coli* suspension. Immediately thereafter, the control group received 0.5 ml saline and the experimental group 0.5 ml of the PL solution i/p. The animals were observed for a period of 12 h and the survivors counted.

The results are summarised in the following table. Each entry represents 1 animal, 12 h denoting that the particular animal survived for the full observation period of 12 h. Other entries denote mortalities at the times indicated, e.g. 2 h inspection (all animals were inspected at 1 h intervals and mortalities counted).

Results

| Control Group | PL-supplemented Group |
|---|---|
| 1h, 1h, 1h, 1h, 1h, 4h | 1h, 3h, 3h, 3h, 12h, 12h |

The results indicate a statistically significant difference in survival rate.

EXAMPLE 27

Cellular Uptake of PL

Fibroblast cell cultures were cultivated in the usual manner in a medium containing different concentrations of various B6 vitamers, and the intracellular PTP content was determined. The results indicated that intracellular PLP levels could be increased by increasing extracellular PN and/or PL concentrations, but that PL was more effective than PN in doing so. Extracellular PTP was not accumulated by the cells. This observation was confirmed by incubating the cells with radioactive PLP: very little radioactivity appeared in the intracellular fraction. When PN was used in the medium, intracellular PLP levels increased much more slowly (and in a time dependent manner) than when PL was used as extracellular source.

When the extracellular PL concentration was 60 nM, intracellular PLP levels reached a concentration of 12 nmol/g cell protein. When extracellular levels were increased, intracellular PLP levels increased correspondingly in an approximately linear fashion until a maximum value of 120 nmol/g cell protein was reached at an extracellular PL concentration of 600 nM. Further increases in intracellular PLP values indicated that cellular PL uptake is a saturable process. Moreover, when both PN and PL were included in the medium, intracellular PLP accumulation was decreased in comparison with PLP accumulation seen when PL alone (in equimolecular concentrations) was included in the medium. This effect was most noticeable in the higher concentration ranges and indicates that high concentrations of PN actually suppress intracellular PLP accumulation.

EXAMPLE 28

Combinations of Pyridoxal With Other Drugs

The following amounts of active substance are formulated with conventional excipients in separate or combined dosage forms:

a) INH tablets
   dosage:
   INH 100 mg 1-2 times daily
   PL 25 mg b) Gentamycin injectable solution

| per ml: | dosage: |
|---|---|
| gentamycin 40 mg | 1-10 ml per day |
| PL 10 mg | monitor by blood level measurement | c) Carbamazepin tablets

| | dosage |
|---|---|
| Carbamazepin 100 mg | 103 tablets/day |
| PL 10 mg | | d) Diphenyl hydantoin tablets

| | dosage |
|---|---|
| PL 100 mg | |
| PL 5 mg | 5 mg/kg daily or as indicated by blood level measurements | d) Dihydralazin tablets

| | dosage: |
|---|---|
| Dihydralazin 25 mg | 1-3 tablets daily |
| PL 10 mg | |

EXAMPLE 29

Dosage rates for oral administration of vitamin B6 derivatives in post-menopausal estrogen formulations

| | Range | | Preferred range | |
|---|---|---|---|---|
| Vitamer | Dose (mg) (daily) | Dose mg/kg bodyweight (daily) | Dose (mg) (daily) | Dose mg/kg bodyweight (daily) |
| PL | 1-200 | 0.02-3.3 | 6-24 | 0.1-0.4 |
| PM | 1-200 | 0.02-3.3 | 6-24 | 0.1-0.4 |
| PLP | 1-240 | 0.02-4.0 | 8-20 | 0.13-5.0 |
| PMP | 1-240 | 0.02-4.0 | 8-20 | 0.13-50 |

EXAMPLE 30

Dosage rates for oral administration of Vitamin B6 vitamers in oral contraceptive formulations

| | Range | | Preferred range | |
|---|---|---|---|---|
| Vitamer | Dose (mg) (daily) | Dose mg/kg bodyweight (daily) | Dose (mg) (daily) | Dose mg/kg bodyweight (daily) |
| PL | 1-60 | 0.02-1 | 4-12 | 0.07-0.2 |
| PM | 1-60 | 0.02-1 | 4-12 | 0.07-0.2 |
| PLP | 1-80 | 0.02-1.3 | 6-15 | 0.1-0.25 |
| PMP | 1-80 | 0.02-1.3 | 6-15 | 0.1-0.25 |

EXAMPLE 31

Oral Contraceptive Tablets Containing Pyridoxal

Active and "placebo" tablets are provided in a combined package, designed as a dispenser prescribing the treatment regimen.

Active Tablets

| Levo-norgestral | 150 micrograms |
|---|---|
| Ethinyl estradiol | 30 micrograms |
| Pyridoxal hydrochloride | 5 mg |
| Excipients | q.s. |

Placebo Tablets

These are formulated in such a manner that each tablet contains 10 mg of PL in an inlet base (e.g. lactose) in such a manner that the placebo tablets resemble the active tablets to encourage overall patient compliance.

Patients are instructed to take one active tablet daily for a period of 21 days (counting from the day on which the menstrual flow commences) followed for a period of 7 days placebo treatment.

PM, PLP or PMP is used as the B6 source as indicated above.

EXAMPLE 32

Estrogen Tablets Containing Pyridoxal Formulation

Tablets containing pyridoxal and estrogen (e.g. as estradiol and/or oestriol) and/or a progestogen are formulated in such a manner that different quantities of each component are administered during 3 consecutive periods of 12, 10 and 6 days as follows:

| Period I (12 days) | Estradiol | 2.2 mg |
|---|---|---|
| | Estriol | 0.8 mg |
| | Pyridoxal.HCl | 12.4 mg |
| | Excipients | qs. |
| Period II (10 days) | Estradiol | 2.2 mg |
| | Estriol | 0.8 mg |
| | Norethisterone acetate | 1.1 mg |
| | Pyridoxal.HCl | 12.4 mg |
| | Excipients | qs. |
| Period III (6 days) | Estradiol | 1.2 mg |
| | Estriol | 0.4 mg |
| | Pyridoxal.HCl | 12.4 mg |
| | Excipients | qs. |

Tablets are presented by means of dispensers which assist patients in following the dosage required precisely.

EXAMPLE 33

Diagnostic Kit and Method for Determining Long Term Disturbance of PN-PLP Pathways—Aspartate Transaminase (AST) Activity The following diagnostic test serves to determine the existence of and the extent of a long term disturbance of the PN-PLP pathway, as may result from: genetic enzymatic defects, or long term elevated levels of vitamin B6 antagonistic drugs: According to the invention the activity of aspartate transaminase (AST), formerly better known as glutamate oxalate transaminase (GOT), in red blood cells are determined as an indicator of such disturbance. AST requires intracellular PLP as a cofactor in order to be active. Accordingly AST activity is a measure of the intracellular PLP concentration. The AST activity is determined either in absolute terms or in relation to total AST present, i.e. after saturation of the AST with PLP, extraneously introduced (as a reagent forming part of the kit) into the hemolysate.

The reagents which are provided in kit form (the inclusion of reagents which are normally available in a laboratory being optional) include the following:

a) As a reagent for hemolizing red blood cells: 10% Triton X-100 (a surfactant), to be used with Tris buffer.

b) As reagents for the production of substrate:
   b1) 0.37 M aspartic acid (4.92 g aspartic acid to appr. 70 ml unbuffered 0.1 M Tris—HCl. Add conc. NaOH to facilitate solubilisation. Adjust pH to 7.2 and volume to 100 ml.
   b2) α-ketoglutarate: 0.0975 g/2.5 ml Tris-HCl (pH 7.2). Enough for 30 determinations.

c) 0.84 mM PLP solution: 11.14 mg PLP/50 ml Tris buffer (optional, if relative AST activity is to be measured, see notes above)

d) Nicotine adenine dinucleotide (reduced form: NADH) as a 0.65 mg/ml solution.

e) Malate dehydrogenase (MDH)

f) 0.1 M Tris-HCl (12.1 g/l). pH should not be adjusted before aspartic acid solution has been prepared (see (b1)).

g) Chemicals for removing hemoglobin:
   standardised 1N HCl
   standardised 1N NaOH
   chloroform Method: Add 100 µl packed red cells to 500 µl Tris buffer and 50 µl 10% Triton X 100 to prepare hemolisate.

To 100 µl of the hemolisate add 420 µl aspartic acid solution, 100 µl PLP or Tris buffer. Preincubate 10 min. at 30° C. Then add 80 µl ketoglutarate and incubate for further 30 min. During this step the AST transaminates the —$NH_2$ moiety from the aspartate to the α-ketoglutarate. In the process aspartate is converted into oxaloacetate (and α-ketoglutanate into glutamate). The amount of oxalo acetate thus produced is a measure of the amount of active AST present in the hemolysate.

At end of incubation period stop reaction as follows and at the same time remove the hemoglobin. Add 500 µl 1N HCl, mix. After 5 min. add 500 ul 1N NaOH. Add 750 µl chloroform, mix thoroughly, centrifuge 15 min. at 4000 r.p.m. This causes denaturation and precipitation of the hemoglobin, leaving a clear aqueous supernatant for spectrophotometric analysis.

Pipet 0.6 ml NADH solution into cuvettes. Add 1.4 ml aqueous supernatant. Record absorbance at 365 nm. Add 8 µl MDH, mix, record absorbance at 365 nm when baseline has stabilised. In this step the oxalo acetate formed in the first step is converted by MDH and NADH into malate, whereby an equimolecular amount of NADH is consumed. The change of absorption at 365 nm (ΔOD) is therefore a measure of the amount of oxaloacetate produced in the first step which in turn reflects the amount of AST present in the hemolysate.

This result is calculated in relation to the hemoglobin in the hemolysate (determined according to the method of Drabkin and Austin (J. Biol. Chem. 1937, Vol. 98, p.719).

An activity index is calculated:

$$\Delta OD \times \frac{1000}{Hb} \times 0.4448 = \mu \text{ mol oxalo acetate/gHb/h}$$

ΔOD = difference of optical densities; Hb = hemoglobin

"Normal" intracellular PLP-levels yield an average activity index of 0.6±6.0 (standard deviation)

Typical depressed values, e.g. after prolonged antagonistic drug use, are exemplified by figures obtained with theophyllin: average 10.4, standard deviation 3.8.

The claims which follow are part of the present disclosure.

What I claim is:

1. A method or raising the intracellular level, other than in a healthy liver, of pyridoxal phosphate (PLP) and the plasma level of pyridoxal (PL) in a human or animal patient having insufficient ability to convert pyridoxine (PN) into intracellular PLP leading to depressed or inadequate intracellular PLP contents, which comprises administering to the patient an active agent selected from the group consisting of pyridoxal (PL), pyridoxamine, acetals or pyridoxal, condensation products arising form the reaction of the aldehyde group or pyridoxal with an amine, and addition salts of any of the foregoing members of the group with pharmaceutically acceptable acids in an amount and at a rate effective to supply from 0.008 to 7.2 mg/kg/day of said active agent, calculated as pyridoxal and based on body weight.

2. The method of claim 1, wherein said active agent is at least one member of the group consisting of pyridoxal itself, pyridoxamine and an addition salt thereof with a pharmaceutically acceptable acid.

3. The method of claim 1, wherein said active agent is at least one member of the group consisting of pyridoxal itself and an addition salt thereof with a pharmaceutically acceptable acid.

4. The method in claim 1, wherein the said amount and the rate is effective to supply up to 1.0 mg/kg/day of the effective agent, calculated as pyridoxal, said active agent being administered by the oral or intravenous route.

5. A method as claimed in claim 1, wherein the pyridoxal or precursor is administered in slow sustained release form.

6. A method as claimed in claim 1, wherein the disturbance of the pathway is measured and the effective amount of composition is administered in accordance with a measurement of the insufficient ability to convert pyridoxine (PN) into intracellular PLP.

7. A method as claimed in claim 6, wherein the disturbance is measured by measuring the oxidase activity in a cell sample.

8. A method as claimed in claim 7, wherein the oxidase activity is measured in erythrocytes by haemolysing under standardised conditions a sample of erythrocytes to prepare a haemolysate, extracting the haemolysate with an organic solvent, clarifying the resulting extract, dissolving the extract in buffer at a pH between 7 and 8, adding a known amount of pyridoxamine or pyridoxine, or the phosphate thereof as a substrate and detecting the ammonia released by the action of the oxidase on the substrate under standardised conditions as a measure of the oxidase content.

* * * * *